US009655643B2

(12) United States Patent
Kahle et al.

(10) Patent No.: US 9,655,643 B2
(45) Date of Patent: *May 23, 2017

(54) BLADELESS OPTICAL OBTURATOR

(71) Applicant: Applied Medical Resources Corporation, Rancho Santa Margarita, CA (US)

(72) Inventors: Henry Kahle, Corona, CA (US); Arkadiusz A. Strokosz, Rancho Santa Margarita, CA (US); Kimball B McGinley, Rancho Santa Margarita, CA (US); Scott V. Taylor, Rancho Santa Margarita, CA (US); Gary M. Johnson, Rancho Santa Margarita, CA (US); John R. Brustad, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 113 days.

This patent is subject to a terminal disclaimer.

(21) Appl. No.: 14/572,134

(22) Filed: Dec. 16, 2014

(65) Prior Publication Data

US 2015/0105728 A1    Apr. 16, 2015

Related U.S. Application Data

(63) Continuation of application No. 14/081,080, filed on Nov. 15, 2013, now Pat. No. 8,940,009, which is a
(Continued)

(51) Int. Cl.
*A61B 17/00* (2006.01)
*A61B 17/34* (2006.01)
(Continued)

(52) U.S. Cl.
CPC ...... *A61B 17/3415* (2013.01); *A61B 17/3417* (2013.01); *A61B 17/3421* (2013.01);
(Continued)

(58) Field of Classification Search
CPC ............ A61B 17/3417; A61B 17/3415; A61B 17/3421; A61B 2017/0046;
(Continued)

(56) References Cited

U.S. PATENT DOCUMENTS

| RE682 E | 4/1859 | Peale |
|---|---|---|
| 184,573 A | 11/1876 | Becker |

(Continued)

FOREIGN PATENT DOCUMENTS

| BE | 1 006 811 | 12/1994 |
|---|---|---|
| CA | 2 170 841 | 9/1997 |

(Continued)

OTHER PUBLICATIONS

U.S. Appl. No. 10/745,262, filed Dec. 23, 2003; Title: "Catheter With Conduit Traversing Tip" (abandoned).
(Continued)

*Primary Examiner* — Victor Nguyen
(74) *Attorney, Agent, or Firm* — Rimas T. Lukas

(57) ABSTRACT

The invention is directed to a bladeless trocar obturator to separate or divaricate body tissue during insertion through a body wall. In one aspect, the obturator of the invention includes a shaft extending along an axis between a proximal end and a distal end; and a bladeless tip disposed at the distal end of the shaft and having a generally tapered configuration with an outer surface, the outer surface extending distally to a blunt point with a pair of side sections having a common shape and being separated by at least one intermediate section, wherein each of the side sections extends from the blunt point radially outwardly with progressive positions
(Continued)

proximally along the axis, and the shaft is sized and configured to receive an optical instrument having a distal end to receive an image of the body tissue. With this aspect, the tapered configuration facilitates separation of different layers of the body tissue and provides proper alignment of the tip between the layers. The side sections include a distal portion and a proximal portion, the distal portion of the side sections being twisted radially with respect to the proximal portion of the side sections. The intermediate section includes a distal portion and a proximal portion, the distal portion of the intermediate section being twisted in a first radial direction and the proximal portion of the intermediate section being twisted in a second radial direction opposite the first radial direction.

14 Claims, 23 Drawing Sheets

Related U.S. Application Data continuation of application No. 13/565,972, filed on Aug. 3, 2012, now Pat. No. 8,608,769, which is a continuation of application No. 13/085,194, filed on Apr. 12, 2011, now Pat. No. 8,267,952, which is a continuation of application No. 10/956,167, filed on Oct. 1, 2004, now Pat. No. 7,947,058, which is a continuation-in-part of application No. 10/489,403, filed as application No. PCT/US02/06759 on Mar. 4, 2002, now Pat. No. 7,686,823.

(60) Provisional application No. 60/324,613, filed on Sep. 24, 2001, provisional application No. 60/508,390, filed on Oct. 3, 2003.

(51) Int. Cl.
*A61B 90/92* (2016.01)
*A61B 17/32* (2006.01)
*A61B 1/313* (2006.01)
*A61B 90/00* (2016.01)

(52) U.S. Cl.
CPC .......... *A61B 17/3496* (2013.01); *A61B 90/92* (2016.02); *A61B 1/3132* (2013.01); *A61B 17/3462* (2013.01); *A61B 17/3474* (2013.01); *A61B 17/3478* (2013.01); *A61B 90/361* (2016.02); *A61B 2017/0046* (2013.01); *A61B 2017/00477* (2013.01); *A61B 2017/00907* (2013.01); *A61B 2017/320044* (2013.01); *A61B 2017/346* (2013.01); *A61B 2017/347* (2013.01); *A61B 2017/3445* (2013.01); *A61B 2017/3456* (2013.01); *A61B 2017/3464* (2013.01); *A61B 2090/3937* (2016.02)

(58) Field of Classification Search
CPC .... A61B 2017/00907; A61B 2017/346; A61B 17/00; A61B 17/34; A61B 17/3496
See application file for complete search history.

(56) References Cited

U.S. PATENT DOCUMENTS

| | | |
|---|---|---|
| 207,932 A | 9/1878 | Alvord |
| 224,513 A | 2/1880 | Burdon |
| 396,754 A | 1/1889 | Mayfield |
| 764,322 A | 7/1904 | Wiegand |
| 1,147,408 A | 7/1915 | Kelis |
| 1,672,258 A | 6/1928 | Hippenmeyer |
| 1,727,495 A | 9/1929 | Wappler |
| 1,845,727 A | 2/1932 | Slaughter |
| 2,024,069 A | 12/1935 | Sharp |
| 2,102,274 A | 12/1937 | Larimore |
| 2,189,343 A | 2/1940 | Fritz |
| 2,301,338 A | 11/1942 | Smith |
| 2,434,594 A | 1/1948 | Schultz |
| 2,441,143 A | 5/1948 | Gracey |
| 2,646,701 A | 7/1953 | Lietin |
| 2,699,770 A | 1/1955 | Fourestier et al. |
| 2,764,148 A | 9/1956 | Sheldon |
| 2,764,149 A | 9/1956 | Sheldon |
| 2,769,355 A | 11/1956 | Henry |
| 2,877,368 A | 3/1959 | Sheldon |
| 2,932,294 A | 4/1960 | Fourestier et al. |
| 3,005,468 A | 10/1961 | Erwin et al. |
| 3,021,834 A | 2/1962 | Sheldon |
| 3,033,226 A | 5/1962 | Allen |
| 3,042,022 A | 7/1962 | Sheldon |
| 3,224,320 A | 12/1965 | Knudsen |
| 3,277,922 A | 10/1966 | Eisel |
| 3,279,460 A | 10/1966 | Sheldon |
| 3,357,433 A | 12/1967 | Fourestier et al. |
| 3,385,553 A | 5/1968 | Braun |
| 3,417,745 A | 12/1968 | Sheldon |
| 3,437,747 A | 4/1969 | Sheldon |
| 3,459,189 A | 8/1969 | Alley et al. |
| 3,556,085 A | 1/1971 | Takahashi |
| 3,613,684 A | 10/1971 | Sheridan |
| 3,653,338 A | 4/1972 | Sauey |
| 3,791,379 A | 2/1974 | Storz |
| 3,817,251 A | 6/1974 | Hasson |
| 3,821,956 A | 7/1974 | Gordhamer |
| 3,870,036 A | 3/1975 | Fiore |
| 3,961,621 A | 6/1976 | Northeved |
| 3,971,385 A | 7/1976 | Corbett |
| 3,994,287 A | 11/1976 | Turp |
| 3,994,301 A | 11/1976 | Agris |
| 4,028,987 A | 6/1977 | Wilson |
| 4,112,932 A | 9/1978 | Chiulli |
| 4,126,291 A | 11/1978 | Gilbert et al. |
| 4,150,929 A | 4/1979 | Brandt |
| 4,168,882 A | 9/1979 | Hopkins |
| 4,180,068 A | 12/1979 | Jacobsen et al. |
| 4,191,191 A | 3/1980 | Auburn |
| 4,222,375 A | 9/1980 | Martinez |
| 4,248,214 A | 2/1981 | Hannah et al. |
| 4,254,762 A | 3/1981 | Yoon |
| 4,269,192 A | 5/1981 | Matsuo |
| 4,274,771 A | 6/1981 | Nishimura |
| 4,285,618 A | 8/1981 | Shanley |
| 4,299,230 A | 11/1981 | Kubota |
| 4,311,138 A | 1/1982 | Sugarman |
| 4,319,563 A | 3/1982 | Kubota |
| 4,356,826 A | 11/1982 | Kubota |
| 4,386,179 A | 5/1983 | Sterling |
| 4,414,966 A | 11/1983 | Stednitz |
| 4,429,856 A | 2/1984 | Jackson |
| 4,436,519 A | 3/1984 | O'Neill |
| 4,493,444 A | 1/1985 | Del Bon et al. |
| 4,498,902 A | 2/1985 | Ash et al. |
| 4,524,805 A | 6/1985 | Hoffman |
| 4,535,773 A | 8/1985 | Yoon |
| 4,535,808 A | 8/1985 | Johanson et al. |
| 4,537,593 A | 8/1985 | Alchas |
| 4,567,882 A | 2/1986 | Heller |
| 4,601,710 A | 7/1986 | Moll |
| 4,607,619 A | 8/1986 | Seike et al. |
| 4,750,877 A | 6/1988 | McFarlane |
| 4,762,130 A | 8/1988 | Fogarty et al. |
| 4,779,613 A | 10/1988 | Hashiguchi et al. |
| 4,803,999 A | 2/1989 | Liegner |
| 4,813,400 A | 3/1989 | Washizuka et al. |
| 4,850,393 A | 7/1989 | Lashomb |
| 4,895,431 A | 1/1990 | Tsujluchi et al. |
| 4,901,142 A | 2/1990 | Ikuno et al. |
| 4,956,143 A | 9/1990 | McFarlane |
| 4,959,067 A | 9/1990 | Muller |
| 4,972,827 A | 11/1990 | Kishi et al. |
| 4,978,350 A | 12/1990 | Wagenknecht |

(56) References Cited

U.S. PATENT DOCUMENTS

| | | |
|---|---|---|
| 5,017,057 A | 5/1991 | Kruygor |
| 5,030,210 A | 7/1991 | Alchas |
| 5,041,100 A | 8/1991 | Rowland et al. |
| 5,057,082 A | 10/1991 | Burchette, Jr. |
| 5,066,288 A | 11/1991 | Deniego et al. |
| 5,098,379 A | 3/1992 | Conway |
| 5,098,388 A | 3/1992 | Kulkashi et al. |
| 5,104,316 A | 4/1992 | McSpadden |
| 5,104,388 A | 4/1992 | Quackenbush |
| 5,104,389 A | 4/1992 | Deem et al. |
| 5,114,407 A | 5/1992 | Burbank |
| 5,116,547 A | 5/1992 | Tsukahara et al. |
| 5,144,942 A | 9/1992 | Decarie et al. |
| 5,147,376 A | 9/1992 | Pianetti |
| 5,159,920 A | 11/1992 | Condon et al. |
| 5,163,941 A | 11/1992 | Garth et al. |
| 5,178,186 A | 1/1993 | Levasseur |
| 5,186,972 A | 2/1993 | Williams et al. |
| 5,197,955 A | 3/1993 | Stephens et al. |
| 5,207,656 A | 5/1993 | Kranys |
| 5,217,441 A | 6/1993 | Shichman |
| 5,221,163 A | 6/1993 | Nishimura |
| 5,240,397 A | 8/1993 | Fay et al. |
| 5,246,425 A | 9/1993 | Hunsberger et al. |
| 5,250,068 A | 10/1993 | Ideguchi et al. |
| 5,256,149 A | 10/1993 | Banik et al. |
| 5,258,003 A | 11/1993 | Ciaglia |
| 5,269,316 A | 12/1993 | Spitainy |
| 5,271,380 A | 12/1993 | Riek et al. |
| 5,279,567 A | 1/1994 | Ciaglia et al. |
| 5,288,290 A | 2/1994 | Brody |
| 5,290,276 A | 3/1994 | Sewell |
| 5,290,585 A | 3/1994 | Elton |
| 5,300,033 A | 4/1994 | Miller |
| 5,334,150 A | 8/1994 | Kaali |
| 5,342,382 A | 8/1994 | Brinkerhoff |
| 5,350,364 A | 9/1994 | Stephens et al. |
| 5,366,446 A | 11/1994 | Tal et al. |
| 5,370,624 A | 12/1994 | Edwards et al. |
| 5,372,588 A | 12/1994 | Farley |
| 5,374,253 A | 12/1994 | Burns, Sr. et al. |
| 5,380,291 A | 1/1995 | Kaali |
| 5,387,197 A | 2/1995 | Smith |
| 5,389,077 A | 2/1995 | Melinyshin et al. |
| 5,391,153 A | 2/1995 | Haber et al. |
| 5,391,248 A | 2/1995 | Brain |
| 5,392,766 A | 2/1995 | Masterson et al. |
| 5,405,328 A | 4/1995 | Vidal et al. |
| 5,407,427 A | 4/1995 | Zhu et al. |
| 5,431,151 A | 7/1995 | Riek et al. |
| 5,441,041 A | 8/1995 | Sauer et al. |
| 5,443,484 A | 8/1995 | Kirsch et al. |
| 5,445,615 A | 8/1995 | Yoon et al. |
| 5,454,791 A | 10/1995 | Tovey et al. |
| 5,480,410 A | 1/1996 | Cuschieri et al. |
| 5,510,065 A | 4/1996 | McFarlane |
| 5,540,711 A | 7/1996 | Kieturakis et al. |
| 5,542,845 A | 8/1996 | Jenkins |
| 5,549,546 A | 8/1996 | Schneider et al. |
| 5,551,947 A | 9/1996 | Kaai |
| 5,562,696 A | 10/1996 | Nobles et al. |
| 5,569,291 A | 10/1996 | Privitera |
| 5,569,292 A | 10/1996 | Scwemberger et al. |
| 5,577,993 A | 11/1996 | Zhu et al. |
| 5,591,186 A | 1/1997 | Wurster et al. |
| 5,591,192 A | 1/1997 | Privitera et al. |
| 5,593,402 A | 1/1997 | Patrick |
| 5,603,720 A | 2/1997 | Kieturakis |
| 5,609,562 A | 3/1997 | Kaali |
| 5,609,604 A | 3/1997 | Schwemberger et al. |
| 5,613,954 A | 3/1997 | Nelson et al. |
| 5,622,462 A | 4/1997 | Gakhar et al. |
| 5,630,805 A | 5/1997 | Ternamian |
| 5,634,908 A | 6/1997 | Loomas |
| 5,658,236 A | 8/1997 | Sauer |
| 5,662,615 A | 9/1997 | Blake, III |
| 5,662,673 A | 9/1997 | Kieturakis |
| 5,676,611 A | 10/1997 | Foster |
| 5,685,820 A | 11/1997 | Riek et al. |
| 5,695,462 A | 12/1997 | Sutcu et al. |
| 5,697,947 A | 12/1997 | Wolf |
| 5,720,730 A | 2/1998 | Blake, III |
| 5,720,761 A | 2/1998 | Kaali |
| 5,735,867 A | 4/1998 | Golser et al. |
| 5,738,628 A | 4/1998 | Sierocuk |
| 5,743,881 A | 4/1998 | Demco |
| 5,746,734 A | 5/1998 | Domandy, Jr. et al. |
| 5,752,970 A | 5/1998 | Yoon et al. |
| 5,759,185 A | 6/1998 | Grinberg |
| 5,779,697 A | 7/1998 | Glowa et al. |
| 5,785,693 A | 7/1998 | Halning |
| 5,792,112 A | 8/1998 | Hart et al. |
| 5,797,888 A | 8/1998 | Yoon et al. |
| 5,797,944 A | 8/1998 | Nobeles et al. |
| 5,817,061 A * | 10/1998 | Goodwin ............ A61B 17/3417 600/121 |
| 5,817,062 A | 10/1998 | Flom et al. |
| 5,836,957 A | 11/1998 | Schulz |
| 5,842,971 A | 12/1998 | Yoon |
| 5,860,996 A | 1/1999 | Urban et al. |
| 5,865,809 A | 2/1999 | Moenning et al. |
| 5,871,474 A | 2/1999 | Hermann et al. |
| 5,876,202 A | 3/1999 | Berlin |
| 5,882,340 A | 3/1999 | Yoon |
| 5,884,639 A | 3/1999 | Chen |
| 5,891,013 A | 4/1999 | Thompson |
| 5,893,865 A | 4/1999 | Swindle |
| 5,904,699 A | 5/1999 | Schwemberger et al. |
| 5,913,818 A | 6/1999 | Co et al. |
| 5,922,351 A | 7/1999 | Daher |
| 5,924,452 A | 7/1999 | Szpapa et al. |
| 5,941,852 A | 8/1999 | Dunlap et al. |
| 5,957,884 A | 9/1999 | Hooven |
| 5,957,888 A | 9/1999 | Hinchliffe |
| 5,968,060 A | 10/1999 | Kellogg |
| 5,976,079 A | 11/1999 | Volz et al. |
| 5,976,168 A | 11/1999 | Chin |
| 5,980,809 A | 11/1999 | Crain et al. |
| 5,984,941 A | 11/1999 | Wilson |
| 6,001,084 A | 12/1999 | Riek |
| 6,007,481 A | 12/1999 | Riek et al. |
| 6,007,544 A | 12/1999 | Kim |
| 6,019,776 A | 2/2000 | Preissman |
| 6,024,551 A | 2/2000 | Yamaguchi |
| 6,030,406 A | 2/2000 | Davis |
| 6,043,310 A | 3/2000 | Liu et al. |
| 6,053,194 A | 4/2000 | Nelson et al. |
| 6,068,637 A | 5/2000 | Popov et al. |
| 6,077,481 A | 6/2000 | Ichida et al. |
| 6,092,551 A | 7/2000 | Bennett |
| 6,168,355 B1 | 1/2001 | Wardell |
| 6,179,528 B1 | 1/2001 | Wardell |
| 6,203,559 B1 | 3/2001 | Davis |
| 6,203,745 B1 | 3/2001 | Wachsmann et al. |
| 6,221,061 B1 | 4/2001 | Engelson et al. |
| 6,228,059 B1 | 5/2001 | Astarita |
| 6,228,063 B1 | 5/2001 | Aboul-Hosn |
| 6,270,484 B1 | 8/2001 | Yoon |
| 6,302,873 B1 | 10/2001 | Moenning |
| 6,319,266 B1 | 11/2001 | Stellon |
| 6,346,074 B1 | 2/2002 | Roth |
| 6,355,014 B1 | 3/2002 | Zadno-Azizi et al. |
| 6,387,043 B1 | 5/2002 | Yoon |
| 6,462,111 B1 | 10/2002 | Singh et al. |
| 6,468,228 B1 | 10/2002 | Topel et al. |
| 6,478,806 B2 | 11/2002 | McFarlane |
| 6,508,759 B1 | 1/2003 | Taylor et al. |
| 6,520,939 B2 | 2/2003 | Lafontaine |
| 6,579,298 B1 | 6/2003 | Bruneau et al. |
| 6,656,160 B1 | 12/2003 | Johnson et al. |
| 6,656,198 B2 | 12/2003 | Tsonton et al. |
| 6,685,630 B2 | 2/2004 | Sauer et al. |
| 6,764,107 B1 | 7/2004 | Obahi et al. |
| 6,770,731 B2 | 8/2004 | Mason et al. |

(56) References Cited

U.S. PATENT DOCUMENTS

| | | |
|---|---|---|
| 6,835,201 B2 | 12/2004 | O'Heeron |
| 6,884,253 B1 | 4/2005 | McFarlane |
| 6,887,194 B2 | 5/2005 | Hart et al. |
| 6,902,541 B2 | 6/2005 | McNally et al. |
| 6,939,296 B2 | 9/2005 | Ewers et al. |
| 7,008,979 B2 | 3/2006 | Schottman et al. |
| 7,037,303 B2 | 5/2006 | Beaufore et al. |
| 7,056,294 B2 | 6/2006 | Khairkhahan et al. |
| 7,056,329 B2 | 6/2006 | Kerr |
| 7,070,586 B2 | 7/2006 | Hart et al. |
| 7,182,752 B2 | 2/2007 | Stubbs |
| 7,344,519 B2 | 3/2008 | Wing et al. |
| 7,370,709 B2 | 5/2008 | Williamson, Jr. |
| 7,470,255 B2 | 12/2008 | Sterns et al. |
| 7,563,250 B2 | 7/2009 | Wenchell |
| 7,686,823 B2 | 3/2010 | Pingleton et al. |
| 7,708,713 B2 | 5/2010 | Albrecht et al. |
| 7,758,603 B2 | 7/2010 | Taylor et al. |
| 7,794,644 B2 | 9/2010 | Taylor et al. |
| 7,811,253 B2 | 10/2010 | Hart et al. |
| 7,942,862 B2 | 5/2011 | Hart et al. |
| 7,947,058 B2 | 5/2011 | Kahle et al. |
| 8,007,477 B2 | 8/2011 | Johnson et al. |
| 8,028,395 B2 | 10/2011 | Taylor et al. |
| 8,075,530 B2 | 12/2011 | Taylor et al. |
| 8,105,285 B2 | 1/2012 | Hart et al. |
| 8,128,590 B2 | 3/2012 | Albrecht et al. |
| 8,152,828 B2 | 4/2012 | Taylor et al. |
| 8,267,952 B2 | 9/2012 | Kahle et al. |
| 8,282,663 B2 | 10/2012 | Smith |
| 8,292,853 B2 | 10/2012 | Hart et al. |
| 8,317,815 B2 | 11/2012 | Mastri et al. |
| 8,377,090 B2 | 2/2013 | Taylor et al. |
| 8,382,663 B2 | 2/2013 | Taylor et al. |
| 8,940,009 B2 * | 1/2015 | Kahle ............ A61B 17/3417 604/264 |
| 2002/0013597 A1 | 1/2002 | McFarlane |
| 2002/0026207 A1 | 2/2002 | Stellon et al. |
| 2002/0133188 A1 | 9/2002 | O'Heeron et al. |
| 2002/0183715 A1 | 12/2002 | Mantell et al. |
| 2002/0183775 A1 | 12/2002 | Tsonton et al. |
| 2003/0023201 A1 | 1/2003 | Aboul-Hosn |
| 2003/0032755 A1 | 2/2003 | Gomey et al. |
| 2003/0059263 A1 | 3/2003 | Chen |
| 2003/0187471 A1 | 10/2003 | Cooper |
| 2004/0015185 A1 | 1/2004 | Ewers et al. |
| 2004/0082969 A1 | 4/2004 | Kerr |
| 2004/0093000 A1 | 5/2004 | Kerr |
| 2004/0093018 A1 | 5/2004 | Johnson et al. |
| 2004/0106942 A1 | 6/2004 | Taylor et al. |
| 2004/0108623 A1 | 6/2004 | Deeter et al. |
| 2004/0167559 A1 | 8/2004 | Taylor et al. |
| 2004/0199127 A1 | 10/2004 | Jensen et al. |
| 2004/0204671 A1 | 10/2004 | Stubbs et al. |
| 2004/0230155 A1 | 11/2004 | Blanco et al. |
| 2004/0230217 A1 | 11/2004 | O'Heeroon |
| 2004/0254517 A1 | 12/2004 | Quiroz-Mercado et al. |
| 2005/0033237 A1 | 2/2005 | Fentress et al. |
| 2005/0033246 A1 | 2/2005 | Ahlberg et al. |
| 2005/0038466 A1 | 2/2005 | O'Heeron et al. |
| 2005/0059865 A1 | 3/2005 | Kahle |
| 2005/0065543 A1 | 3/2005 | Kahle et al. |
| 2005/0107803 A1 | 5/2005 | Guanche |
| 2005/0107816 A1 | 5/2005 | Pingleton et al. |
| 2005/0113533 A1 | 5/2005 | Shaikh et al. |
| 2005/0149094 A1 | 7/2005 | Kashara et al. |
| 2005/0149096 A1 | 7/2005 | Hilal et al. |
| 2005/0159711 A1 | 7/2005 | Kathrani et al. |
| 2005/0216028 A1 | 9/2005 | Hart et al. |
| 2005/0227610 A1 | 10/2005 | Zukor et al. |
| 2005/0273133 A1 | 12/2005 | Schluzas et al. |
| 2005/0283122 A1 | 12/2005 | Nordgren |
| 2005/0288622 A1 | 12/2005 | Albrecht et al. |
| 2006/0030755 A1 | 2/2006 | Ewers et al. |
| 2006/0030870 A1 | 2/2006 | Staudner |
| 2006/0041270 A1 | 2/2006 | Lenker et al. |
| 2006/0047284 A1 | 3/2006 | Gresham |
| 2006/0058570 A1 | 3/2006 | Rapach et al. |
| 2006/0074374 A1 | 4/2006 | Gresham |
| 2006/0118189 A1 | 6/2006 | Trekulve et al. |
| 2006/0224174 A1 | 10/2006 | Smith et al. |
| 2006/0264991 A1 | 11/2006 | Johnson |
| 2007/0027453 A1 | 2/2007 | Hart et al. |
| 2007/0075465 A1 | 4/2007 | Taylor et al. |
| 2007/0088277 A1 | 4/2007 | McGinley |
| 2007/0239108 A1 | 10/2007 | Albrecht et al. |
| 2008/0065021 A1 | 3/2008 | Jenkins et al. |
| 2008/0086074 A1 | 4/2008 | Taylor et al. |
| 2008/0086093 A1 | 4/2008 | Steppe et al. |
| 2009/0030375 A1 | 1/2009 | Franer et al. |
| 2009/0137943 A1 | 5/2009 | Stearns et al. |
| 2009/0187079 A1 | 7/2009 | Albrecht et al. |
| 2009/0281500 A1 | 11/2009 | Acosta et al. |
| 2010/0025045 A1 | 2/2010 | Lake et al. |

FOREIGN PATENT DOCUMENTS

| | | |
|---|---|---|
| DE | 0365049 | 12/1922 |
| DE | 1616107 | 4/1971 |
| DE | 2218901 | 10/1973 |
| DE | 2538758 | 3/1977 |
| DE | 2929233 | 1/1980 |
| DE | 2922239 | 12/1980 |
| DE | 4020956 | 1/1991 |
| DE | 4133073 | 4/1992 |
| DE | 4035146 | 5/1992 |
| DE | 4116648 | 11/1992 |
| DE | 29503750 | 4/1995 |
| DE | 29521431 | 4/1997 |
| DE | 19541041 | 5/1997 |
| DE | 19718086 | 11/1998 |
| DE | 19819432 | 11/1999 |
| EP | 0135364 | 3/1985 |
| EP | 0312787 | 4/1989 |
| EP | 0347140 | 12/1989 |
| EP | 0369936 | 5/1990 |
| EP | 0369937 | 5/1990 |
| EP | 0474124 | 3/1992 |
| EP | 0548612 | 6/1993 |
| EP | 0556056 | 8/1993 |
| EP | 0664992 | 8/1995 |
| EP | 0724864 | 8/1996 |
| EP | 1074224 | 2/2001 |
| EP | 1582158 | 10/2005 |
| EP | 2229897 | 9/2010 |
| EP | 2233090 | 9/2010 |
| FR | 1370580 | 8/1964 |
| GB | 2 124 970 | 2/1984 |
| GB | 186 005 | 9/1992 |
| GB | 2 313 316 | 11/1997 |
| JP | 408127661 | 5/1996 |
| JP | 2001-137253 | 5/2001 |
| SU | 0942730 | 7/1982 |
| SU | 1328658 | 8/1987 |
| SU | 1329769 | 8/1987 |
| WO | WO 93/25148 | 12/1993 |
| WO | WO 94/11040 | 5/1994 |
| WO | WO 96/01074 A2 | 1/1996 |
| WO | WO 96/01132 | 1/1996 |
| WO | WO 96/10361 | 4/1996 |
| WO | WO 97/40758 | 11/1997 |
| WO | WO 98/33536 | 8/1998 |
| WO | WO 99/02089 | 1/1999 |
| WO | WO 99/15084 | 4/1999 |
| WO | WO 00/18306 | 4/2000 |
| WO | WO 00/54648 | 9/2000 |
| WO | WO 01/01847 | 1/2001 |
| WO | WO 01/01871 | 1/2001 |
| WO | WO 01/08563 | 2/2001 |
| WO | WO 02/01998 | 1/2002 |
| WO | WO 02/34108 | 5/2002 |
| WO | WO 02/41795 | 5/2002 |
| WO | WO 03/026512 | 4/2003 |
| WO | WO 03/032819 | 4/2003 |

(56) References Cited

FOREIGN PATENT DOCUMENTS

| WO | WO 03/096879   | 11/2003 |
|----|----------------|---------|
| WO | WO 2004/037097 | 5/2004  |
| WO | WO 2004/093699 | 11/2004 |
| WO | WO 2005/063134 | 7/2005  |
| WO | WO 2007/093957 | 8/2007  |

OTHER PUBLICATIONS

Co-Pending U.S. Appl. No. 12/750,372, filed Mar. 30, 2010, title: "Bladeless Obturator".
Co-Pending U.S. Appl. No. 11/549,872, filed Oct. 16, 2006, title: "Surgical Devices, Systems and Methods Thereof Having Gel Material, Gel Coatings, or Gel Lubricants".
Co-Pending U.S. Appl. No. 13/565,972, filed Aug. 3, 2012, title: "Bladeless Optical Obturator".
Co-Pending U.S. Appl. No. 13/356,260, filed Jan. 23, 2012, title: "Insufflating Optical Surgical Instrument".
Co-Pending U.S. Appl. No. 13/078,750, filed Apr. 1, 2011 title "Surgical Access Apparatus and Method".
Co-Pending U.S. Appl. No. 12/569,652, filed Sep. 29, 2009; title "First-Entry Trocar System".
Co-Pending U.S. Appl. No. 12/359,964, filed Jan. 26, 2009, title: "Insufflating Access System".
Co-Pending U.S. Appl. No. 13/462,330, filed May 2, 2012, title: "Low-Profile Surgical Universal Access Port".
Co-Pending U.S. Appl. No. 13/411,244, filed Mar. 2, 2012, title: "Blunt Tip Obturator".
Co-Pending U.S. Appl. No. 13/586,825, filed Aug. 15, 2012, title: "Blunt Tip Obturator".
Co-Pending U.S. Appl. No. 11/868,883, filed Oct. 8, 2007; Title: "Visual Insufflation Port".
International Bureau of WIPO, International Preliminary Report on Patentability for International Application No. PCT/US04/032346, dated May 20, 2008.
International Bureau of WIPO, International Preliminary Report on Patentability for International Application No. PCT/US2005/022716 mailed Nov. 22, 2005.
International Bureau of WIPO, International Preliminary Report on Patentability for International Application No. PCT/US2006/060013, mailed Apr. 24, 2008.
International Bureau of WIPO, The International Preliminary Report on Patentability for International Application No. PCT/US2009/058792, titled First Entry Trocar System, dated Mar. 29, 2011.
International Bureau of WIPO, The International Preliminary Report on Patentability for International Application No. PCT/US2007/080724, titled "Visual Insufflation Port", dated Apr. 7, 2009.
International Bureau of WIPO, The International Preliminary Report on Patentability for International Application No. PCT/US2009/32026, titled "Insufflating Access System", dated Jul. 27, 2010.
International Bureau of WIPO, The International Preliminary Report on Patentability for International Application No. PCT/US2004/000695, titled "Surgical Access Apparatus and Method", dated Jul. 22, 2005.
International Bureau of WIPO, The International Preliminary Report on Patentability for International Application No. PCT/US2004/04883, titled "Surgical Access Apparatus and Method", dated Sep. 9, 2005.
International Searching Authority, International Search Report and Written Opinion for International Application No. PCT/US2004/000695, titled "Surgical Access Apparatus and Method", mailed Jan. 12, 2005.
International Searching Authority, International Search Report and Written Opinion for International Application No. PCT/US2004/04883, titled "Surgical Access Apparatus and Method", mailed Mar. 31, 2005.
International Searching Authority, International Search Report and Written Opinion for International Application No. PCT/US2002/06759, titled "Bladeless Obturator", mailed Jul. 12, 2002.
International Searching Authority, International Search Report and Written Opinion for International Application No. PCT/US2005/022716, titled "Insufflating Optical Surgical Instrument", mailed Nov. 22, 2005.
International Searching Authority, International Search Report and Written Opinion for International Application No. PCT/US04/32346, titled Bladeless Optical Obturator, mailed May 20, 2008.
International Searching Authority, International Search Report and Written Opinion for International Application No. PCT/US2009/32026, titled "Insufflating Access System", mailed Mar. 23, 2009.
International Searching Authority, International Search Report and Written Opinion for International Application No. PCT/US2007/080724, titled "Visual Insufflation Port", mailed Apr. 16, 2008.
International Searching Authority/US, International Search Report and The Written Opinion of the International Searching Authority dated May 27, 2009, for International Application No. PCT/US2009/037863, titled "Instrument Seal with Inverting Shroud", mailed May 27, 2009.
The International Searching Authority, The International Search Report and the Written Opinion for International Application No. PCT/US2009/058792, titled "First Entry Trocar System", mailed Dec. 23, 2009.
International Searching Authority, International Search Report and Written Opinion for International Application No. PCT/US2012/036119, title "Low-Profile Surgical Universal Access Port", mailed Nov. 7, 2012.
European Patent Office, Supplementary European Search Report for European Patent Application No. EP 04 70 1731 based on International Application No. PCT/US2004/000695, titled "Surgical Access Apparatus and Method", dated Apr. 11, 2007.
European Patent Office, Supplementary European Search Report for European Patent Application No. EP 02706494.8, titled "Bladeless Obturator", dated Jun. 24, 2008.
European Patent Office, Supplementary European Search Report for European Patent Application No. EP 03753017.7, titled "Blunt Tip Obturator", dated Nov. 21, 2008.
European Patent Office, Supplementary European Search Report for European Patent Application No. EP 04712378, titled "Surgical Access Apparatus and Method", dated May 19, 2008.
European Patent Office, Supplementary European Search Report for European Patent Application No. EP 07843973.4, titled "Visual Insufflation Port" dated Oct. 4, 2008.
European Patent Office, Supplementary European Search Report for European Patent Application No. EP 04793965.7, titled "Bladeless Optical Obturator", dated Apr. 16, 2010.
European Patent Office, Supplementary European Search Report for European Patent Application No. EP 11154547.1, titled "Blunt Tip Obturator", dated Mar. 22, 2011.
European Patent Office, European Search Report for European Application No. 11191191.3, titled "Bladeless Obturator" dated Feb. 29, 2012.
European Patent Office, European Search Report for European Application No. 11191179.8, titled "Bladeless Obturator", dated Feb. 21, 2012.
European Patent Office, European Search Report for European Application No. 11191193.9, titled "Bladeless Obturator", dated Mar. 5, 2012.
European Patent Office, European Search Report for European Application No. 11191187.1, titled Bladeless Obturator, dated Feb. 23, 2012.
European Patent Office, European Search Report for European Application No. 11191184.8, titled "Bladeless Obturator", dated Feb. 23, 2012.
European Patent Office, European Search Report for European Application No. 11191189.7, titled "Bladeless Obturator", dated Feb. 24, 2012.
European Patent Office, European Search Report for European Application No. 11191175.6, titled "Bladeless Obturator", dated Feb. 21, 2012.

(56) References Cited

OTHER PUBLICATIONS

European Patent Office, European Search Report for European Application No. 047017314, titled "Surgical Access Apparatus and Method", dated Mar. 30, 2007.
Taut, Inc., ADAPT—Asymmetrical Dilating Access Port, Geneva Illinois.
Karl Storz, The Karl Storz Ternamian EndoTIP (TM) System, date: Aug. 27, 2001.
Karl Storz, Zerocart Trocar with eccentric tip, Recklinghausen, Germany, date Mar. 7, 2001.
Ethicon Endo-Surgery, Inc., Endopath Minimally Invasive Access, date: 2001.
European Patent Office, Invitation to Pay Additional Fees for International Application No. PCT/US2012/036119, titled "Low-Profile Surgical Universal Access Port", mailed Jul. 13, 2012.
European Patent Office, European Search Report for European Application No. 12187933, titled "Insufflating Optical Surgical Instrument", dated Nov. 20, 2012.
European Patent Office, European Search Report for European Application No. 12187929, titled "Insufflating Optical Surgical Instrument", dated Nov. 20, 2012.
European Patent Office, European Search Report for European Application No. 12186716.2, titled "Bladeless Optical Obturator", dated Mar. 7, 2013.
European Patent Office, European Search Report for European Application No. 12186717.0, titled "Bladeless Optical Obturator", dated Mar. 7, 2013.
European Patent Office, European Search Report for European Application No. 12186712.1, titled "Bladeless Optical Obturator", dated Mar. 7, 2013.
European Patent Office, European Search Report for European Application No. 12186720.4, titled "Bladeless Optical Obturator", dated Mar. 7, 2013.
International Searching Authority, International Search Report and Written Opinion for International Application No. PCT/US2013/023458 titled "Adaptable Obturator for Various Sized Trocars", mailed Mar. 19, 2013.
European Patent Office, European Search Report for European Application No. 12186722.0, titled "Bladeless Optical Obturator", dated Mar. 20, 2013.
European Patent Office, European Search Report for European Application No. 12186721.2, titled "Bladeless Optical Obturator", dated Mar. 22, 2013.
European Patent Office, European Search Report for European Application No. 12186723.8, titled "Bladeless Optical Obturator", dated Mar. 22, 2013.
European Patent Office, European Communication pursuant to Article 94(3) EPC for European Patent Application No. 12186717 .0, titled "Bladeless Optical Obturator", dated Mar. 26, 2013.
Yang, Guoqing, Hong Jun, Zhu, Linbo, Li Baotong, Xiong Meihua, and Wang Fei, Chinese Journal of Mechanical Engineering, (vol. 26, No. 3,2013), Three-Dimensional Finite Element Analysis of the Mechanical Properties of Helical Threat Connection, Received Jun. 7, 2012, Revised Jan. 28, 2013, Accepted Feb. 27, 2013.
European Patent Office, European Search Report for European Application No. 15163037.3, titled "Bladeless Optical Obturator" dated Jul. 30, 2015 (7 pgs.).

* cited by examiner

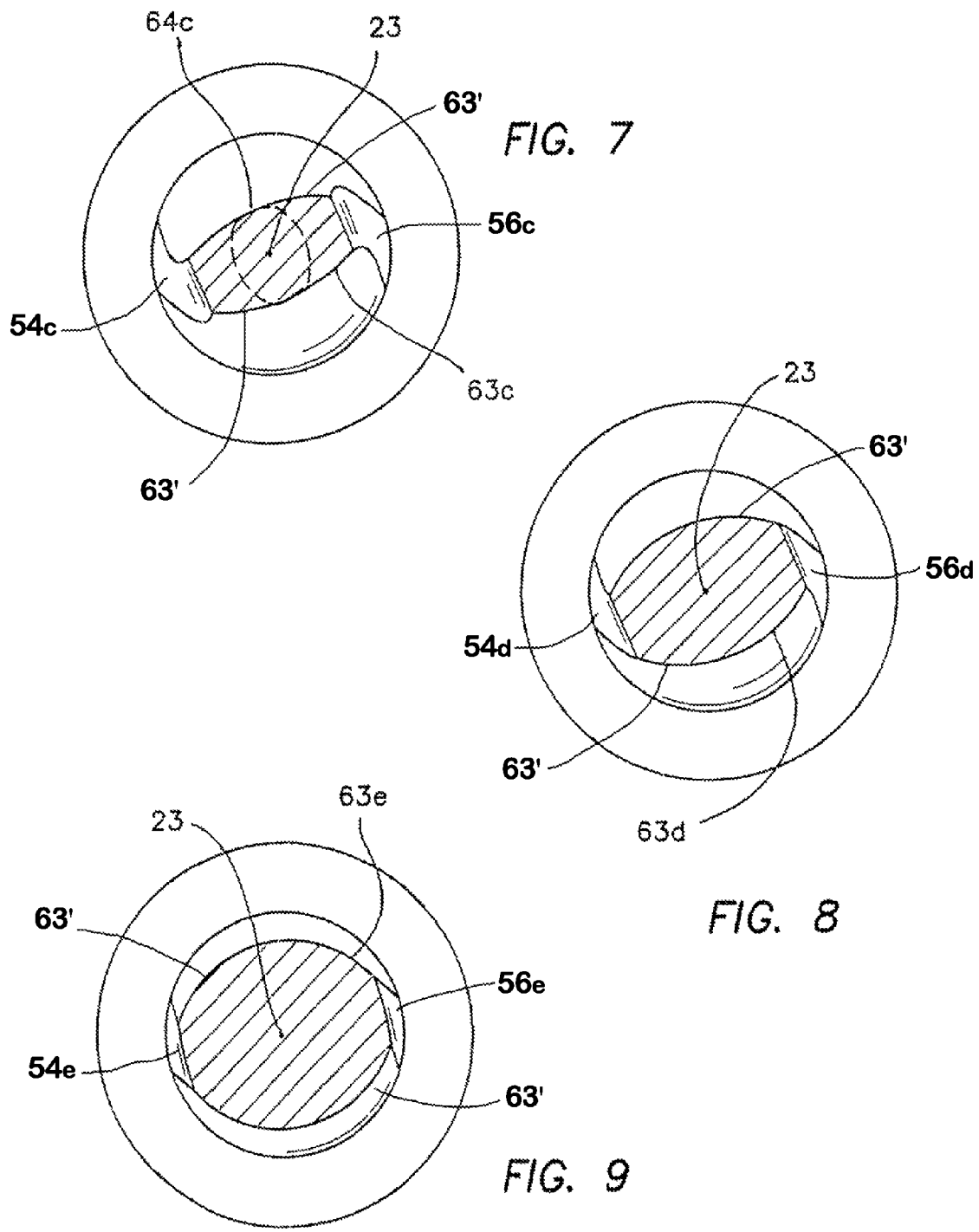

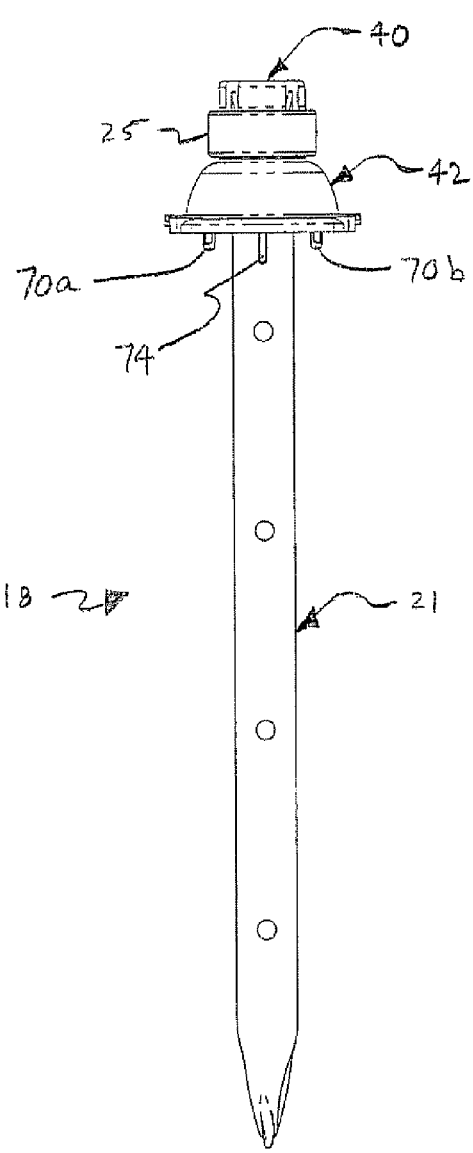
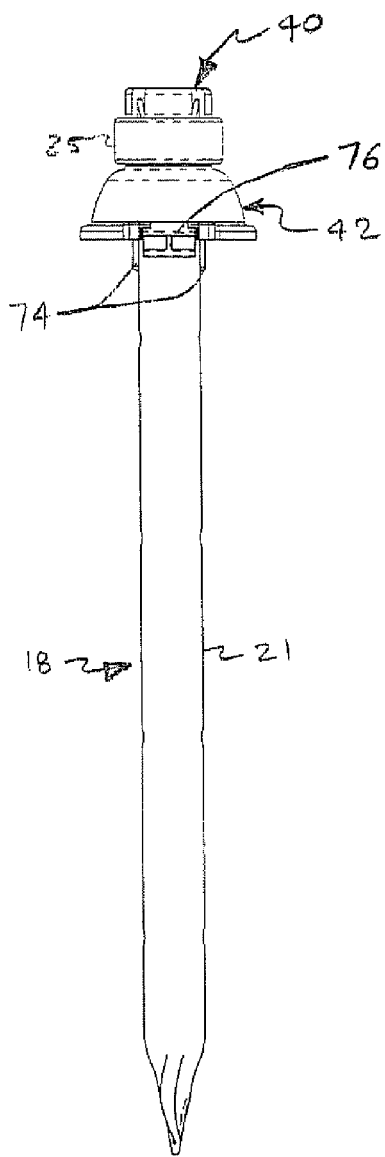
FIG. 20
FIG. 21

BLADELESS OPTICAL OBTURATOR

CROSS-REFERENCE TO RELATED APPLICATIONS

This application is a continuation of co-pending U.S. patent application Ser. No. 14/081,080 entitled "Bladeless optical obturator" filed on Nov. 15, 2013 which is a continuation of U.S. patent application Ser. No. 13/565,972 entitled "Bladeless optical obturator" filed on Aug. 3, 2012 now U.S. Pat. No. 8,608,769 which is a continuation of U.S. patent application Ser. No. 13/085,194 entitled "Bladeless optical obturator" filed on Apr. 12, 2011 now U.S. Pat. No. 8,267,952 which is a continuation of U.S. patent application Ser. No. 10/956,167 entitled "Bladeless optical obturator" filed on Oct. 1, 2004 now U.S. Pat. No. 7,947,058 which is continuation-in-part of U.S. application Ser. No. 10/489,403, filed on Mar. 11, 2004, now U.S. Pat. No. 7,686,823, which is a 371 of International Application No. PCT/US02/06759, filed on Mar. 4, 2002 based on Provisional Application Ser. No. 60/324,613, filed on Sep. 24, 2001, and entitled "Bladeless obturator," all of which are fully incorporated herein by reference in their entireties. U.S. patent application Ser. No. 10/956,167 entitled "Bladeless optical obturator" filed on Oct. 1, 2004 and now U.S. Pat. No. 7,947,058 further claims priority to provisional application Ser. No. 60/508,390, filed on Oct. 3, 2003, entitled "Bladeless optical obturator," which is fully incorporated herein by reference in its entirety.

BACKGROUND OF THE INVENTION

Field of the Invention

This invention generally relates to trocar systems including obturators and, more specifically, to blunt tip obturators having hollow shafts for insertion of optical instruments.

Discussion of the Prior Art

Trocar systems have been of particular advantage in facilitating less invasive surgery across a body wall and within a body cavity. This is particularly true in abdominal surgery where trocars have provided a working channel across the abdominal wall to facilitate the use of instruments within the abdominal cavity.

The trocar systems of the past typically included a cannula, which provides the working channel, and an obturator which is used to place the cannula across the abdominal wall. The obturator is inserted into the working channel of the cannula and then pushed through the abdominal wall with a penetration force of sufficient magnitude resulting in penetration of the abdominal wall. Once the cannula is in place, the obturator can be removed.

Obturators have been developed with an attempt to reduce the penetration force of the abdominal wall. For example, sharp blades, sharp edges and piercing points have typically been used to enable the obturator to cut or pierce its way through the abdominal wall. While the sharp blades, sharp edges and piercing points have facilitated a reduced penetration force, they have also caused larger trocar site defects. These trocar site defects may have to be sutured closed resulting in increased operating room costs and procedural time. Moreover, once the abdominal wall has been penetrated, the sharp blades, sharp edges and piercing points of the obturator may still cause damage to the vessels and organs that lie within the peritoneal cavity. For example, the blades on the obturators that serve to cut tissue during insertion may also cut vessels or puncture organs that may result in patient injury or surgical complications.

In some cases, shields have been provided with the obturators in order to sense penetration of the abdominal wall and immediately shield the sharp blades, edges or piercing points. These shielding systems are typically complex and require some time to deploy and, as such, many have not been effective in protecting the vessels and organs against the sharp blades, edges or piercing points. Accordingly, there remains a need in the art for an improved bladeless obturator that separates tissue during insertion through a body wall. Moreover, there is a need for a transparent blunt tip obturator having a hollow shaft to enable insertion of an optical instrument to view the insertion of the obturator through the body wall.

SUMMARY OF THE INVENTION

The invention is directed to a bladeless trocar obturator to separate or divaricate body tissue during insertion through a body wall. The distal tip of the bladeless obturator is constructed of a transparent material to enable visualization of tissue during the insertion of the obturator through the body wall. The bladeless obturator is configured to enable the insertion of a conventional laparoscope which typically includes an imaging element and fiber optic light fibers. During use, the bladeless obturator is first inserted into and through a trocar seal and cannula. A conventional laparoscope is then inserted into the proximal end of the bladeless obturator and advanced to the distal tip of the obturator. An endoscopic video camera is attached to the proximal end of the laparoscope and the bladeless trocar system is then axially advanced by the surgeon through the body wall, the surgeon can visually observe the tissue as it is being separated via a video monitor that is connected to the endoscopic video camera.

In one aspect, the obturator of the invention comprises a shaft extending along an axis between a proximal end and a distal end; and a bladeless tip disposed at the distal end of the shaft and having a generally tapered configuration with an outer surface, the outer surface extending distally to a blunt point with a pair of side sections having a common shape and being separated by at least one intermediate section, wherein each of the side sections extends from the blunt point radially outwardly with progressive positions proximally along the axis, and the shaft is sized and configured to receive an optical instrument having a distal end to receive an image of the body tissue. With this aspect, the tapered configuration facilitates separation or spreading of different layers of the body tissue and provides proper alignment of the tip between the layers. The side sections include a distal portion and a proximal portion, the distal portion of the side sections being twisted radially with respect to the proximal portion of the side sections. The intermediate section includes a distal portion and a proximal portion, the distal portion of the intermediate section being twisted in a first radial direction and the proximal portion of the intermediate section being twisted in a second radial direction opposite the first radial direction.

The bladeless tip can be formed from a transparent material or a translucent material. The bladeless tip can be formed from a plastic material or a glass material. The plastic material can be at least one of polycarbonate, polyphenylsulfone, polyetherimide, acrylic, and polyvinyl chloride. The bladeless obturator can be constructed such that at least one of the shaft and the tip is formed from a reusable or a disposable material. The reusable material can be a metallic material or an autoclavable polymer. The bladeless tip can be generally hollow or substantially solid to receive the distal end of the optical instrument. The bladeless tip can also be solid. The bladeless tip can further comprise at least one portion that is marked differently from the rest of the tip to serve as an indicator, for example, of depth as the tip is being inserted into the body tissue. The bladeless tip can be shaped and configured to receive the distal end of the optical instrument having an angled or non-angled lens. The bladeless tip can further comprise a ledge to provide proper positioning of the distal end of the optical instrument having an angled or non-angled lens. The bladeless tip can further comprise a bulbous section to accommodate the distal end of the angled lens optical instrument. The bladeless tip can be further coated or formed from a soft elastomeric material. The shaft and the tip can be connected together by adhesive bonding, ultrasonic welding, snap-fitting, with a shrink tube, or by overmolding the tip over the shaft. The bladeless tip can further comprise a cutout section to provide the distal end of the optical instrument with direct vision of the body tissue.

In another aspect of the invention, the bladeless obturator further comprises a lock disposed at the proximal end of the shaft to frictionally lock the optical instrument in an axial position in the shaft. The lock operates to prevent the optical instrument from moving axially relative to the shaft while allowing the optical instrument to rotate freely about the shaft. The lock can be constructed from a plastic material including polycarbonate. The lock can be a multi-finger collet having an inner diameter smaller than an outer diameter of the optical instrument wherein the fingers of the collet spread open during insertion of the optical instrument providing frictional engagement with the outer diameter of the optical instrument. The lock can further comprise a camming member to constrict the optical instrument in the axial position relative to the shaft. The camming member may be a horizontal or vertical camming member. In another aspect, the lock can further comprise a locking collar to rotationally lock the optical instrument. In yet another aspect, the lock can further comprise a locking nut and thread that frictionally engage the optical instrument in the axial position relative to the shaft, or an elastomeric element that facilitates frictional engagement with the optical instrument in the axial position relative to the shaft.

In another aspect of the invention, the bladeless obturator further comprises a cap disposed at the proximal end of the shaft. The cap may further comprise a handle.

In yet another aspect of the invention, a surgical obturator adapted to separate body tissue is disclosed comprising a shaft extending along an axis between a proximal end and a distal end; and a bladeless tip disposed at the distal end of the shaft having a tapered surface forming proximally into an outer surface, the outer surface including a pair of generally opposed sections, wherein the outer surface has a generally geometric shape in progressive radial cross-sections from a distal cross-section to a proximal cross-section, wherein the pair of generally opposed sections of the outer surface appears as a pair of lines in each of the progressive radial cross-sections, wherein at least one of the pair of lines becomes more arcuate in the progressive radial cross-sections, and wherein the shaft is sized and configured to receive an optical instrument having a distal end to receive an image of the body tissue. With this aspect, the area of the geometric shape increases along the progressive radial cross-sections.

In another aspect of the invention, a surgical obturator adapted to separate body tissue is disclosed comprising a shaft having a proximal end and a distal end; and a transparent bladeless tip disposed at the distal end of the shaft having a tapered surface forming proximally into an outer surface, the outer surface extending distally to a blunt point, wherein the shaft is sized and configured to receive an optical instrument having a distal end to receive an image of the body tissue.

In yet another aspect of the invention, an optical separator adapted to receive an image of a body tissue and to separate the body tissue is disclosed comprising an optical instrument having a proximal end and a distal end; and a bladeless tip removably attached at the distal end of the optical instrument and having a generally tapered configuration with an outer surface, the outer surface extending distally to a blunt point.

These and other features of the invention will become more apparent with a discussion of the various embodiments in reference to the associated drawings.

DESCRIPTION OF THE DRAWINGS

The accompanying drawings, which are included in and constitute a part of this specification, illustrate the embodiments of the invention and, together with the description, explain the features and principles of the invention. In the drawings:

FIG. 7 is a radial cross-section view taken along line 7-7 of FIG. 2;

FIG. 8 is a radial cross-section view taken along line 8-8 of FIG. 2;

FIG. 9 is a radial cross-section view taken along line 9-9 of FIG. 2;

FIGS. 20 and 21 illustrate side views of a bladeless obturator of the invention having a laparoscope lock;

DESCRIPTION OF THE INVENTION

Figure 1A:
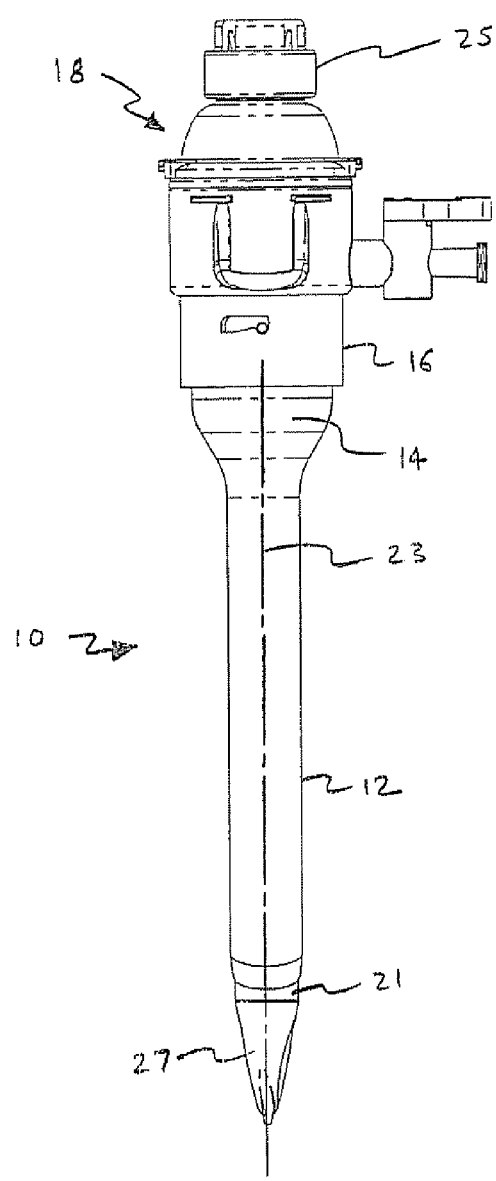
FIGS. 1A and 1B illustrate side views of a trocar system including a cannula with associated valve housing, and an obturator with a blunt tip extending through the working channel of the cannula to facilitate placement across the abdominal wall.
Figure 1B:
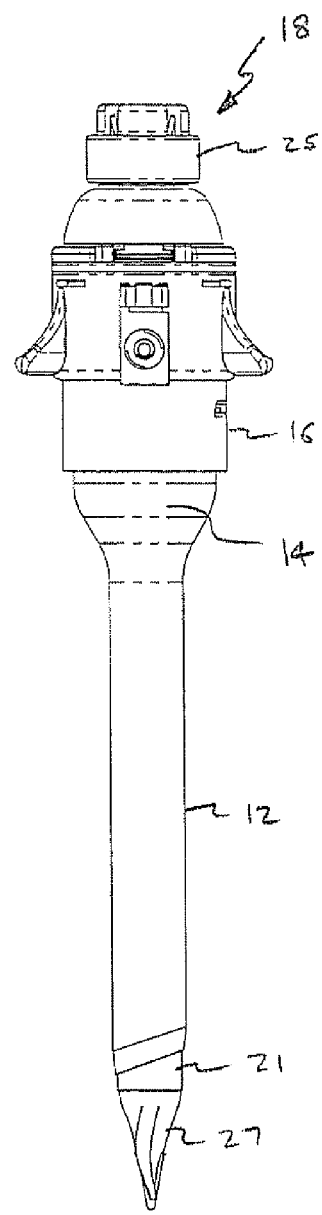

A trocar system is illustrated in FIG. 1 and is designated by reference numeral 10. This system includes a cannula 12, defining a working channel 14, and a valve housing 16. The system 10 also includes an obturator 18 having a shaft 21 extending along an axis 23. A handle 25 is disposed at a proximal end of the shaft 21 while a blunt tip 27 is disposed at a distal end of the shaft 21. The shaft 21 of the obturator 18 is sized and configured for disposition within the working channel 14 of the cannula 12. With this disposition, the obturator 18 can be placed across a body wall such as the abdominal wall to provide the cannula 12 with access across the wall and into a body cavity, such as the peritoneal or abdominal cavity. The blunt tip 27 serves to direct the obturator 18 through the abdominal wall and the peritoneum, and can be removed with the obturator 18 once the cannula 12 is operatively disposed with the working channel 14 extending into the abdominal cavity. The diameter of the shaft 21 can range from about 3 mm to about 20 mm and is designed to fit within a trocar seal and the cannula 12.

In accordance with the present invention, the tip 27 is provided with a blunt tip configuration. The blunt tip 27 of the invention takes into account the anatomical configuration of the abdominal wall with an improved structural design and method of insertion. To fully appreciate these aspects of the invention, it is helpful to initially discuss the anatomy associated with the abdominal wall. The abdominal wall typically includes a skin layer and a series of muscle layers, in addition to fat and fascia. The muscle layers are each defined by muscle fibers that extend generally parallel to each other in a direction that is different for each of the layers. For example, fibers of a first muscle layer and a second muscle layer may extend in directions that are generally 90 degrees off of each other.

Having noted the directional nature of the muscle fibers, it can be appreciated that such a structure may be separated or divaricated by an obturator having a blunt tip. The blunt tip may also include a twisted rectangular configuration to facilitate movement between the muscle fibers and layers. That is, the blunt tip is capable of being moved generally parallel to and between the fibers associated with a particular muscle layer.

As described earlier, the fibers of the muscle layers may be oriented at different angles to each other such that proper alignment of the tip 27 for separation of one layer may not necessarily result in proper alignment for separation of the next layer. For at least this reason, the obturator 18 has a blunt tip 27 to direct the obturator 18 through the different layers and a rectangular configuration that is twisted slightly so that separation of a first layer begins to rotate the distal end of the blunt tip 27 into proper orientation for separation of the next layer.

The twisted configuration of the blunt tip 27 also causes the blunt tip 27 to function, for example, with the mechanical advantage of a screw thread. With this configuration, an exemplary method of placement requires that the user grip the handle 25 of the obturator 18 and twist it about the axis 23. This twisting motion in combination with the screw configuration of the blunt tip 27 converts radial movement into forward movement along the axis 23. Thus, the user applies both a forwardly directed force as well as a radial force to move the trocar system 10 in a forward direction.

Figure 2:
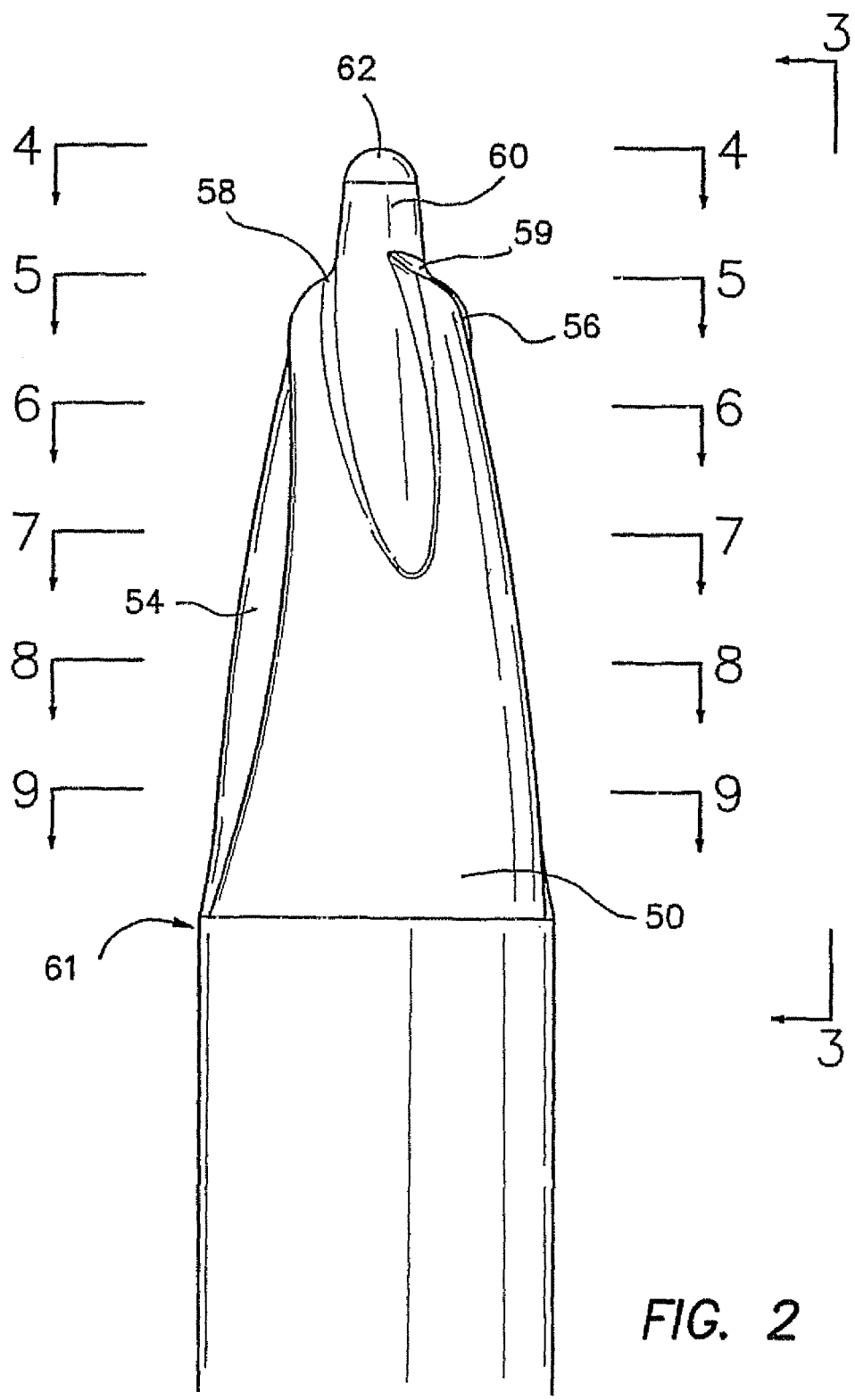
FIG. 2 is a side elevation view of the blunt tip of the obturator of the invention.
Figure 3:
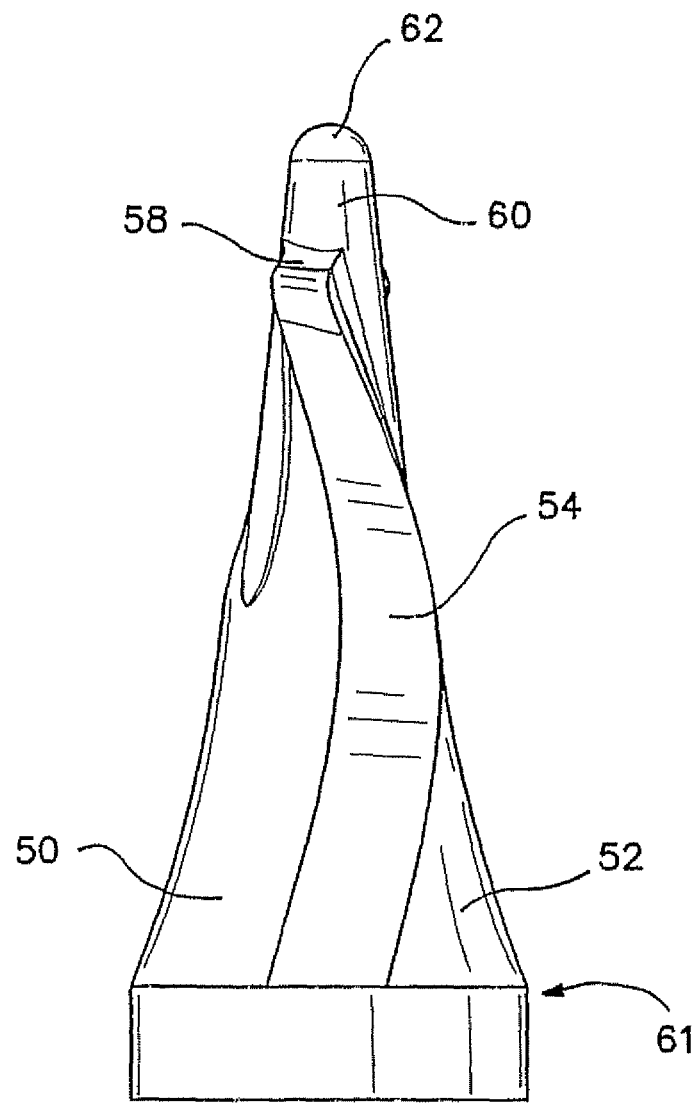
FIG. 3 is a side elevation view of the blunt tip taken along line 3-3 of FIG. 2.

The twisted configuration of the blunt tip 27 is most apparent in the side elevation views of FIGS. 2 and 3. In this embodiment, the blunt tip 27 comprises generally of eight surfaces: two opposing surfaces 50 and 52, separated by two side surfaces 54 and 56, two end surfaces 58 and 59, a generally tapered surface 60 formed in surfaces 50 and 52 around axis 23 and extending beyond end surfaces 58 and 59, and a blunt surface 62.

Figure 4:
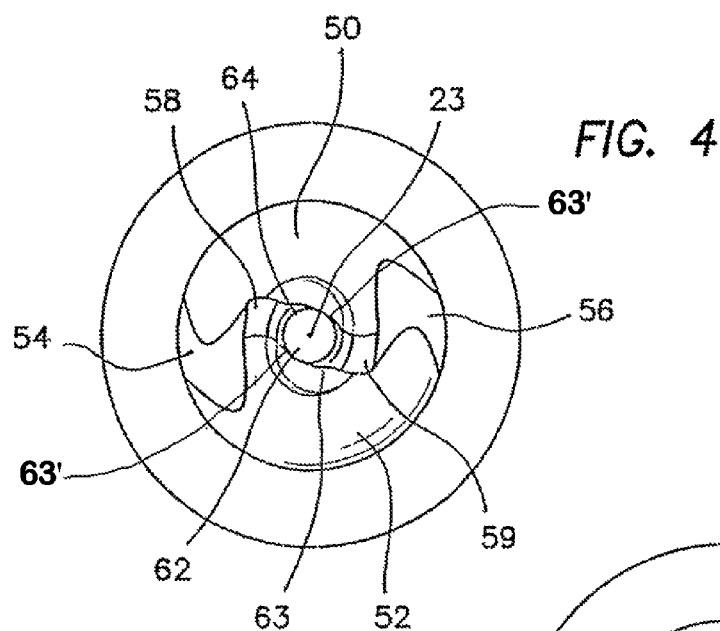
FIG. 4 is an end view taken along line 4-4 of FIG. 2.

The surfaces 50 and 52, side surfaces 54 and 56, and tapered surface 60 generally define the cross-section of the blunt tip 27 from blunt surface 62 to proximal end 61. This configuration can best be appreciated with reference to the cross-section views of FIGS. 4-9. In FIG. 4, the distal end of the blunt tip 27 is shown with a circle 64 having the smallest circular area and a rectangle 63 having the greatest length-to-width ratio. The rectangle 63 has a twisted, S-shaped configuration at end surfaces 58 and 59.

As views are taken along progressive proximal cross-sections, it can be seen that the circle 64 becomes larger and the rectangle 63 becomes less twisted, and the width increases relative to the length of the rectangle 63. The spiral nature of the blunt tip 27 is also apparent as the circle 64 and rectangle 63 move counterclockwise around the axis 23. This is perhaps best appreciated in a comparison of the circle 64, the rectangle 63 and the side surfaces 54 and 56 in FIG. 6 relative to that in FIG. 5. With progressive proximal positions, the circle 64 begins to expand with increasing circular area and the rectangle 63 begins to widen with a reduction in the ratio of length to width. The long sides 63' of the rectangle 63 also tend to become more arcuate as they approach a more rounded configuration most apparent in FIGS. 8 and 9. That is, the circle 64 and the rounded rectangle 63 become more circular with progressive proximal positions. Furthermore, the circle 64 expands at a lesser rate than the rectangle 63, which eventually absorbs the circle 64 as shown in FIGS. 8 and 9. In these figures, it will also be apparent that the rotation of the rectangle 63 reaches a most counterclockwise position and then begins to move clockwise. This is best illustrated in FIGS. 7-9. This back and forth rotation results from the configuration of the side surfaces 54 and 56, which in general are U-shaped as best illustrated in FIGS. 2 and 3.

The ratio of the length to width of the rectangle 63 is dependent on the configuration of the side surfaces 54 and 56, which define the short sides of the rectangle 63 as well as the configuration of the surfaces 50 and 52, which define the long sides of the rectangle 63. Again with reference to FIGS. 2 and 3, it can be seen that the side surfaces 54 and 56 are most narrow at the end surfaces 58 and 59. As the side surfaces 54 and 56 extend proximally, they reach a maximum width near the point of the most counterclockwise rotation, shown generally in FIG. 8, and then reduce in width as they approach the proximal end 61. Along this same distal to proximal path, the surfaces 50 and 52 transition from a generally flat configuration at the end surfaces 58 and 59 to a generally rounded configuration at the proximal end 61.

Figure 5:
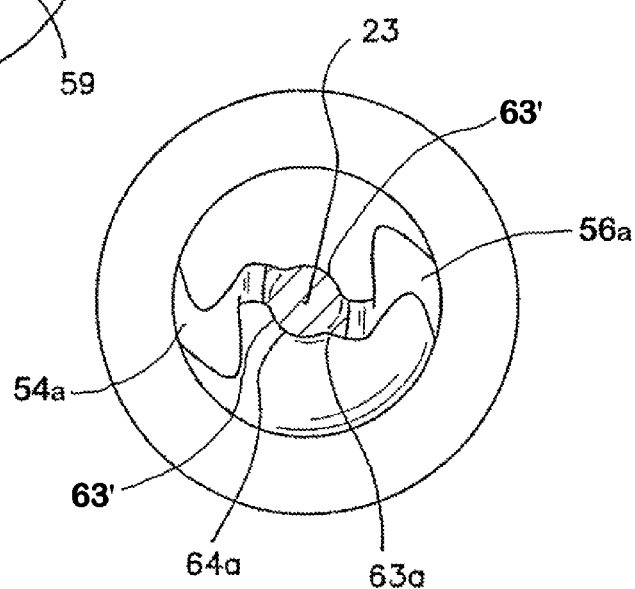
FIG. 5 is a radial cross-section view taken along line 5-5 of FIG. 2.
Figure 6:
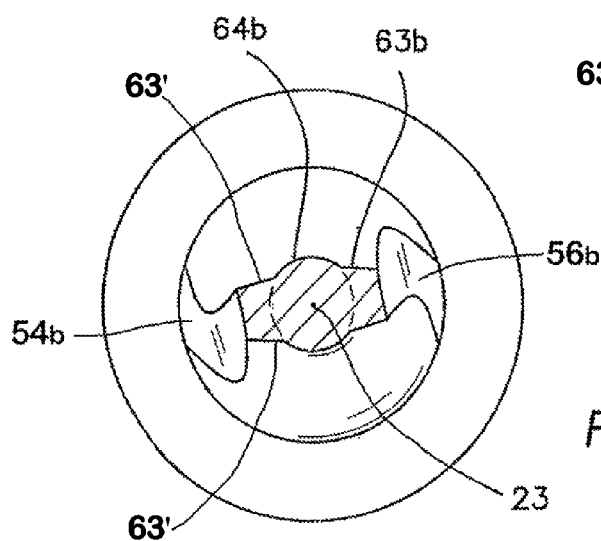
FIG. 6 is a radial cross-section view taken along line 6-6 of FIG. 2.
Figure 10:
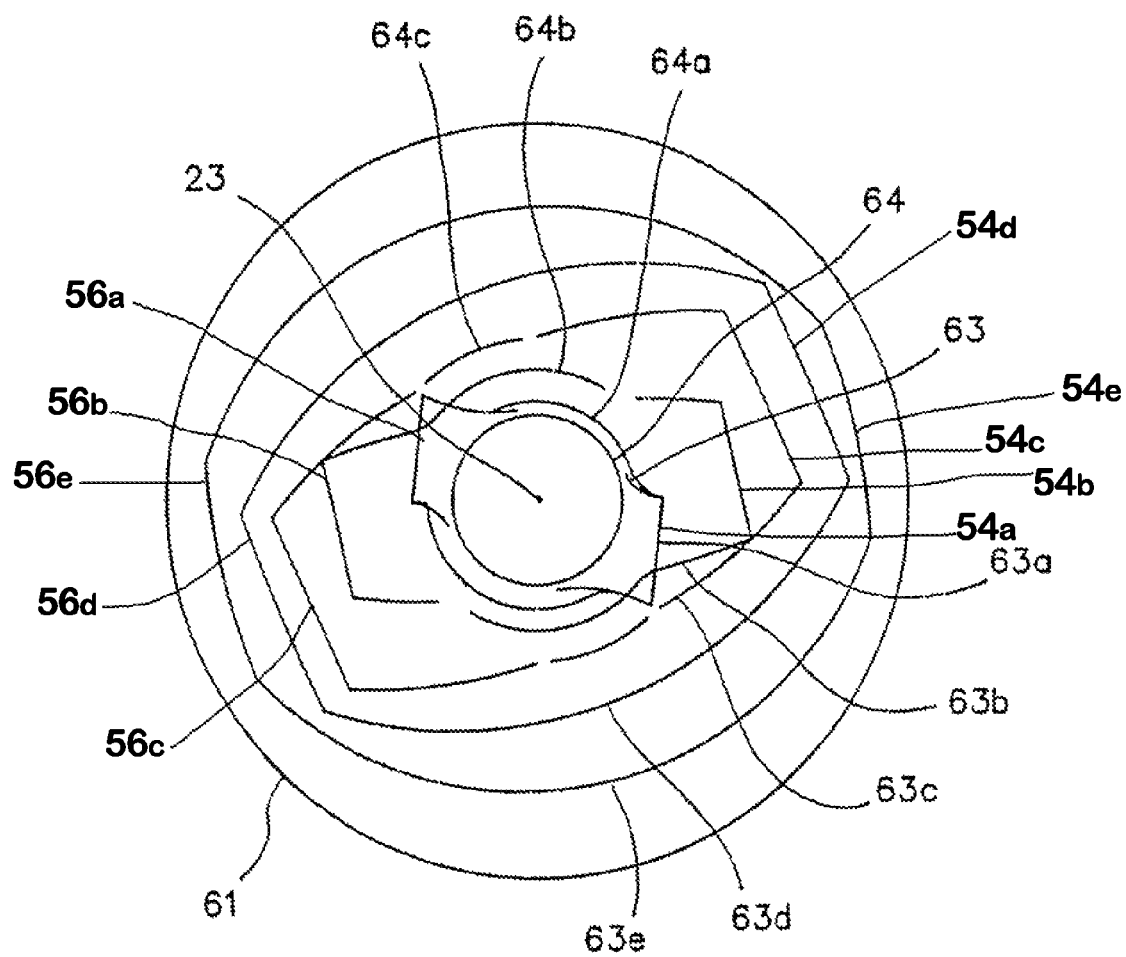
FIG. 10 is a schematic view illustrating each of the FIGS. 4-9 super-imposed to facilitate an understanding of the blunt tip and its twisted configuration.

In the progressive views of FIGS. 5-7, the circle 64 is further designated with a lower case letter a, b or c, respectively; similarly, the rectangle 63 and the side surfaces 54 and 56 are further designated with a lower case letter a, b, c, d or e, respectively, in FIGS. 5-9. In FIG. 10, the circles 64, 64a-64c, the rectangles 63, 63a-63e and the side surfaces 54, 54a-54e and 56, 56a-56e are superimposed on the axis 23 to show their relative sizes, shapes and angular orientations.

With a generally tapered configuration at the distal end and a rectangular configuration at a distal portion of the tip, the tip 27 appears much like a flathead screwdriver having a blunt tip. More particularly, the tip 27 includes a tapered structure extending outward from the end surfaces 58 and 59 that serves to direct the obturator 18 through the tissue fibers.

In one aspect, the lengths of the end surfaces 58 and 59 may be aligned parallel with the fibers of each muscle layer. A simple back and forth twisting motion of the blunt tip 27 tends to separate the fibers along natural lines of separation, opening the muscle layer to accept the larger diameter of the cannula 12. Once the first layer is substantially separated, the tapered and twisted configuration of the blunt tip 27 directs and turns the rectangle 63 more into a parallel alignment with fibers in the next layer. Again, the blunt tip 27 and the twisting or dithering motion facilitates an easy separation of the fibers requiring a significantly reduced insertion force.

The invention facilitates a unique method of separating tissue and can be applied to any object with a blunt tip and generally flat sides. In particular, the device of the invention can be operated by rotating in alternating clockwise and counterclockwise directions while applying a downward force. When rotating in alternating directions, the tissue is moved apart and a larger opening is created for a profile of greater cross-sectional area to follow. This process continues safely as the device enters the peritoneal cavity and moves to its operative position.

Figure 11:
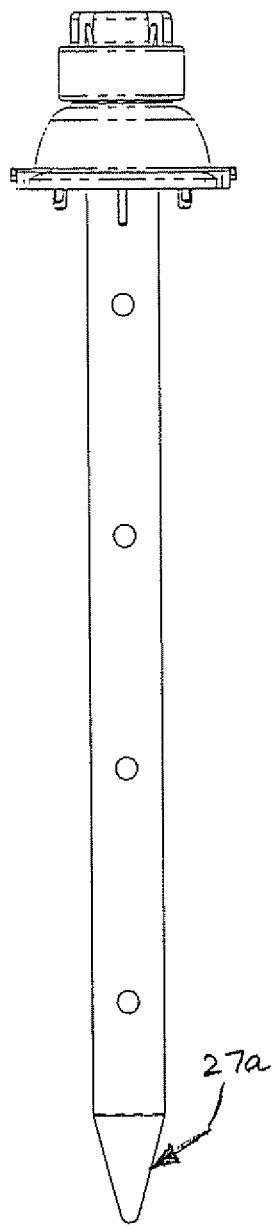
FIG. 11 illustrates a side view of a bladeless obturator of the invention having a tip formed as a blunt tapered shape.
Figure 12:
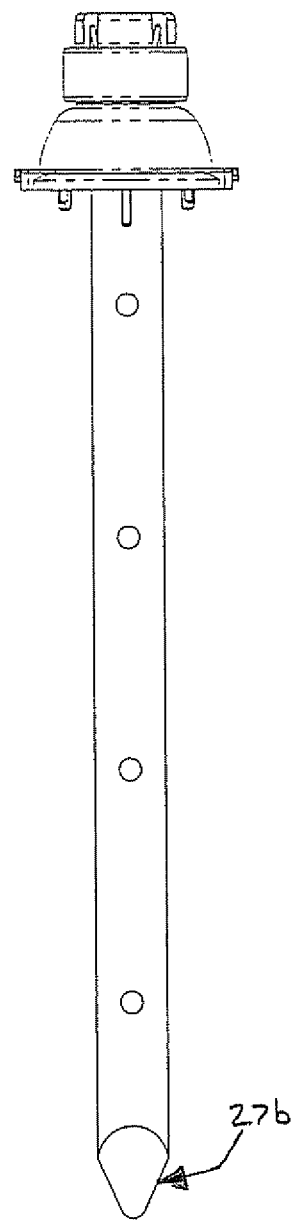
FIG. 12 illustrates a side view of a bladeless obturator of the invention having a tip formed as a pyramidal shape.
Figure 13:
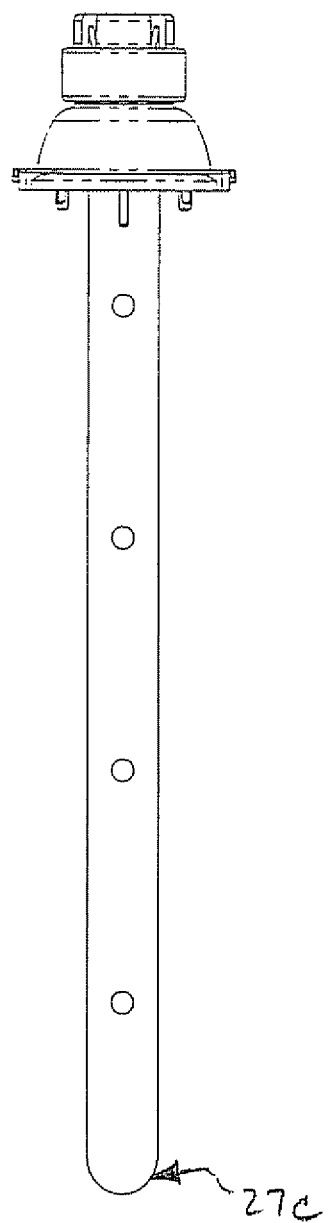
FIG. 13 illustrates a side view of a bladeless obturator of the invention having a fully radiused tip.

When the cannula 12 is ultimately removed, the size of the opening left in the tissue is minimal. Importantly, this opening is left with a small defect that does not require suturing due to a dilating effect caused by the mere separation of fibers. Since there are no sharp blades, sharp edges or piercing points to cut tissue fibers, the healing process is shortened. It is appreciated that in other aspects of the invention, the tip of the bladeless obturator 18 can be formed as a generally tapered shape 27a with a blunt distal end as illustrated in FIG. 11, as a pyramidal shape 27b with a blunt distal end and blunt edges as illustrated in FIG. 12, and as a fully radiused tip 27c for insertion through flaccid tissue or an existing body orifice such as the urethra as illustrated in FIG. 13.

The blunt tip 27 can be formed from a translucent or a transparent material. The blunt tip 27 can be formed from a plastic material or a glass material. In one aspect, the shaft 21 and the tip 27 are formed from a transparent polycarbonate material.

Figure 14:
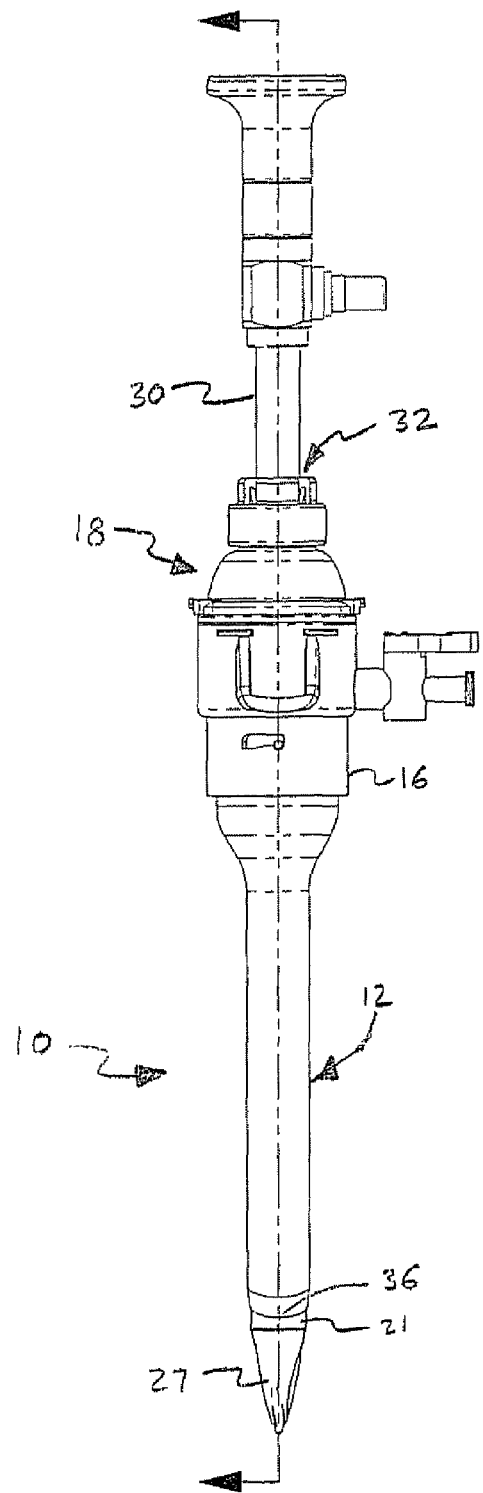
FIGS. 14 and 15 illustrate a side view and a cross-section view, respectively, of the trocar system of FIGS. 1A and 1B and further illustrating the insertion of a laparoscope.
Figure 15:
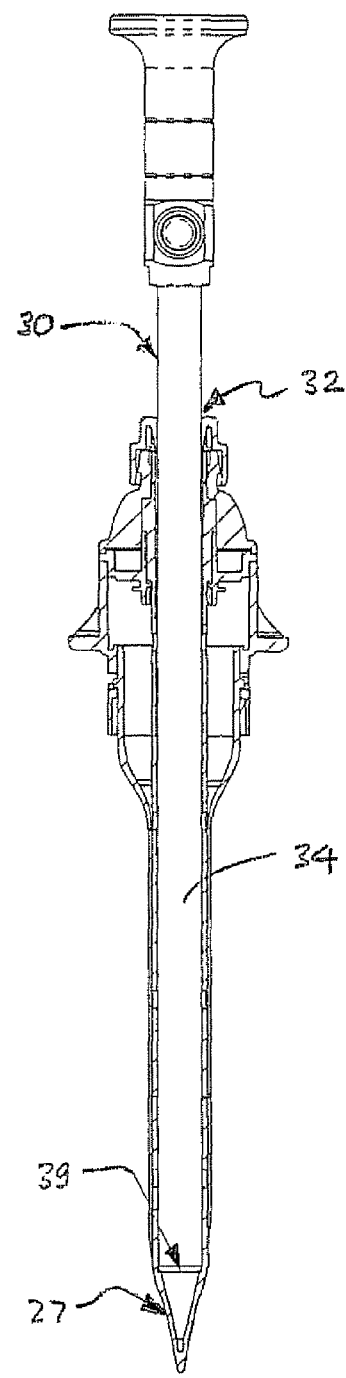

Referring to FIGS. 14 and 15, the bladeless obturator 18 of the invention is designed to accommodate the insertion of a conventional laparoscope 30. In particular, the shaft 21 of the bladeless obturator 18 is hollow to allow for the insertion of the laparoscope 30 at an opening 32. The shaft 21 is sized and configured to allow the laparoscope 30 to slide within proximity of the tip 27 thus providing a viewing area through the tip 27. An endoscopic video camera (not shown) is typically connected to the laparoscope 30 and this combination is connected to a video monitor. By enabling the positioning of the conventional laparoscope 30 within the tip 27 of the bladeless obturator 18, it is possible to visually observe body tissue as it is being separated by the trocar system 10. Visualization of body tissue as it is being separated by the trocar system 10 allows a surgeon to monitor the advancement of the trocar system 10 and to avoid traumatizing vessels or organs. For example, during a laparoscopic cholecystectomy, a trocar is usually placed through the umbilicus of the patient. The placement of this trocar is typically performed in a blind fashion in that the surgeon cannot see where the tip of the trocar is as it is advanced through the abdominal wall and into the abdominal cavity of the patient. This results in a high degree of risk that the trocar may be inadvertently advanced too far into the abdomen of the patient resulting in trauma to vital organs and/or vessels. By providing a trocar system with visualization properties, this risk is diminished as the surgeon is better able to determine when the trocar has traversed the abdominal wall.

It is appreciated that the tip 27 may be generally hollow or it may be substantially solid to receive the distal end of the laparoscope 30. In another aspect, the tip 27 may be a solid tip. The tip 27 may further comprise at least one portion that is marked differently from the rest of the tip to serve as an indicator, for example, of depth as the tip 27 is being inserted into the body tissue. The at least one portion may be opaque or marked with a different color from the rest of the tip 27.

The shaft 21 and the tip 27 of the bladeless obturator 18 can accommodate a laparoscope with a non-angled lens, also known as a 0° laparoscope. The shaft 21 and the tip 27 can also accommodate a laparoscope with an angled lens such as a 30° laparoscope. The tip 27 is designed such that when either a 0° laparoscope or a 30° laparoscope is inserted therein, the lens of the laparoscope extends beyond a distal edge 36 of the cannula 12 thereby providing a clear and unobstructed view through the tip 27. The tip 27 further includes a ledge 39 that properly engages either the 0° laparoscope or the 30° laparoscope.

It should be noted that conventional trocars with visualization properties typically require a 0° laparoscope for insertion of the trocars and a 30° laparoscope for viewing anatomical structures during the remainder of the laparoscopic procedure. This requires the operating staff to provide two laparoscopes for the laparoscopic procedure, which increases hospital inventory costs and surgical preparation costs relating to cleaning and sterilization of the laparoscopes. In addition, because two laparoscopes are required for the laparoscopic procedure, there is additional operating room time required during the surgical procedure to transfer the endoscopic video camera from the 0° laparoscope to the 30° laparoscope which results in increased operating room costs for the hospital.

Figure 16:
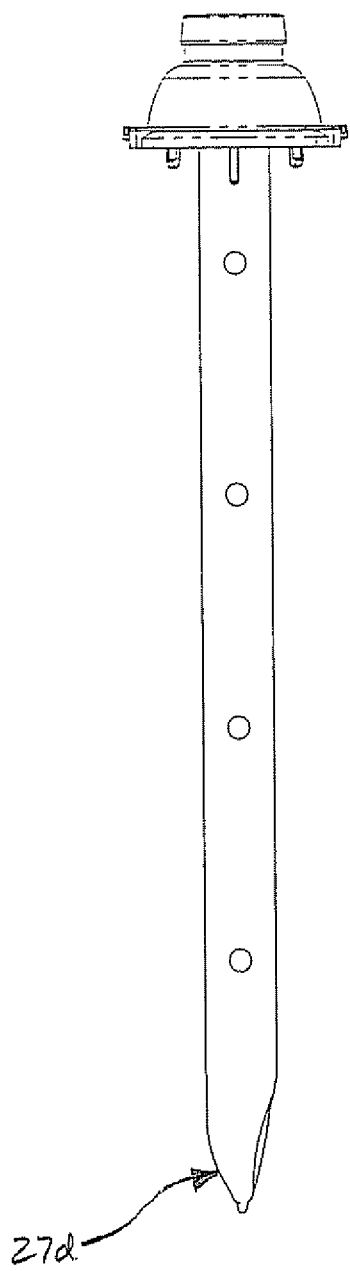
FIG. 16 illustrates a side view of a bladeless obturator of the invention having a bulbous tip.

The bladeless obturator of the present invention provides a clear unobstructed view of body tissue through either a 0° or a 30° laparoscope, therefore obviating the need for a hospital to carry the additional inventory required to provide two laparoscopes for each laparoscopic surgical procedure, and obviating the need for a hospital to clean and sterilize a second laparoscope for each laparoscopic surgical procedure, and obviating the need to transfer the endoscopic video equipment from one laparoscope to the other laparoscope during each laparoscopic surgical procedure. Referring to FIG. 16, the shaft 21 may include a tip with a bulbous section 27d to better accommodate the distal end of the angled lens laparoscope. By adding the bulbous section 27d, the distal end of the angled lens laparoscope would be closer to the tip of the obturator thereby improving visualization.

In yet another aspect of the invention, the bladeless obturator can include integral fiber optic light fiber elements and an integral imaging element within the shaft and the tip of the obturator. The bladeless obturator with integral imaging means can be formed of reusable or disposable materials.

The bladeless obturator 18 can be constructed as a single component or as multiple components such as the shaft 21 and the tip 27. If the obturator 18 is constructed as a single component, then it can be formed from either disposable or reusable materials. If the obturator 18 is constructed as two or more components, then each component can be formed from either disposable or reusable materials as desired for a particular configuration. In one aspect, the obturator 18 is constructed from a single reusable material such as metal (e.g., stainless steel) or an autoclavable polymer to facilitate re-sterilization. In another aspect, the obturator 18 is formed from a transparent steam sterilizable reusable plastic material such as polyphenylsulfone or polyetherimide. The blunt tip 27 can also be coated or otherwise constructed from a soft elastomeric material. In such a case, the material can be a solid elastomer or composite elastomer/polymer.

It is further appreciated that the shaft 21 can be formed so as to be partially or fully flexible. With this configuration, the obturator 18 can be inserted through a passageway containing one or more curves of virtually any shape. A partially or fully flexed obturator 18 can then be used with a flexible cannula 12 allowing greater access to an associated body cavity.

The obturator 18 can include a separately molded tip 27 and a molded or extruded shaft 21 with the two components, as explained above, comprising of the same material or different materials. The tip 27 can then be attached to the shaft 21 by adhesive bonding, ultrasonic welding, snap-fitting, or with a shrink tube. The tip 27 can also be overmolded over the shaft 21 to mechanically lock the two components together. The tip 27 can be formed from a transparent material such as polycarbonate to enable visualization while the shaft 21 can be formed from either an opaque material or a transparent material. The shaft 21 can also be formed from a metal material.

In another aspect, the obturator 18 can include a disposable tip that is releasably attached to a reusable shaft 21. In this aspect, a new tip 27 can be used for each procedure to provide optimal visualization through the tip 27 of the obturator 18 during each procedure.

Figure 17:
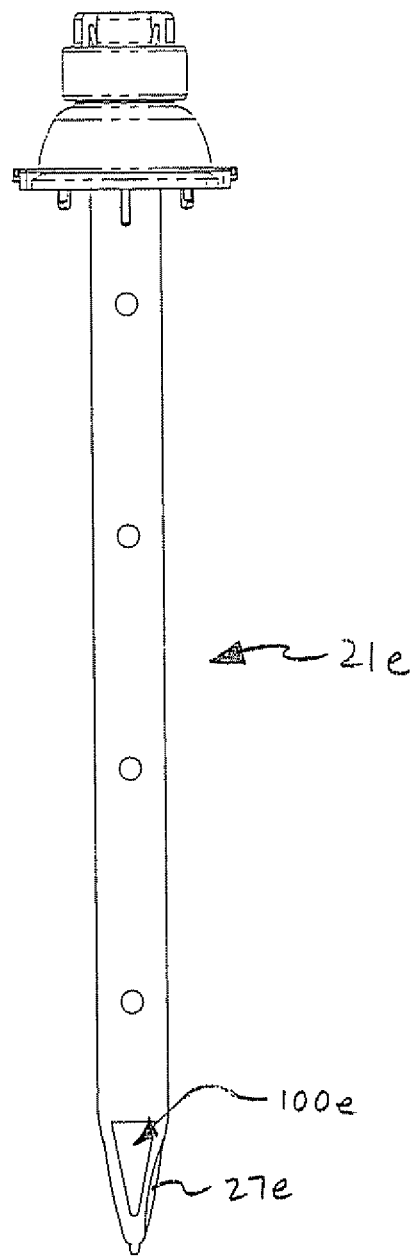
FIG. 17 illustrates a side view of a bladeless obturator of the invention having a tip with a cutout section.

Referring to FIG. 17, there is shown a shaft 18e in accordance with another aspect of the invention including a cutout section 100e in the tip portion 27e that enables direct visualization of the body tissue as the tip 27e separates tissue fibers. By providing an obturator with cutout sections, the reflection of light from the laparoscope is minimized and the visibility of the tissue through the laparoscope is improved as compared to a design where visualization occurs through a plastic or glass window. It is appreciated that the shaft 21e can include a single or a plurality of cutouts 100e in the tip 27e or along the shaft of the obturator.

Figure 18:
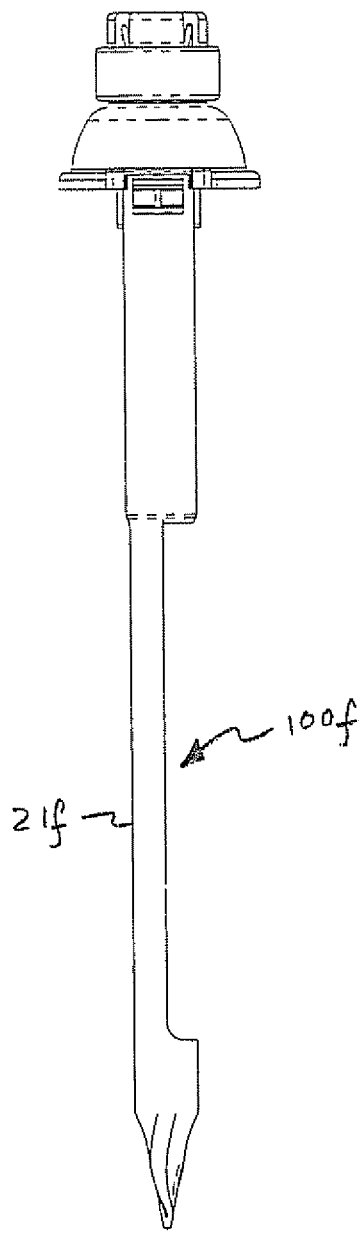
FIG. 18 illustrates a side view of a bladeless obturator of the invention having a shaft with a cutout section.

Referring to FIG. 18, there is shown a shaft 21f in accordance with another aspect of the invention having a cutout portion 100f along the axial axis of the shaft 21f. The shaft 21f has a cross-section of about ½-circle to about ¾-circle and the cutout portion 100f has a cross-section of about ½-circle to about ¼-circle. An advantage of this aspect of the invention is the wall of the shaft 21f can be a little thicker as a result of the cutout section, which makes injection molding of the shaft easier.

Figure 19:
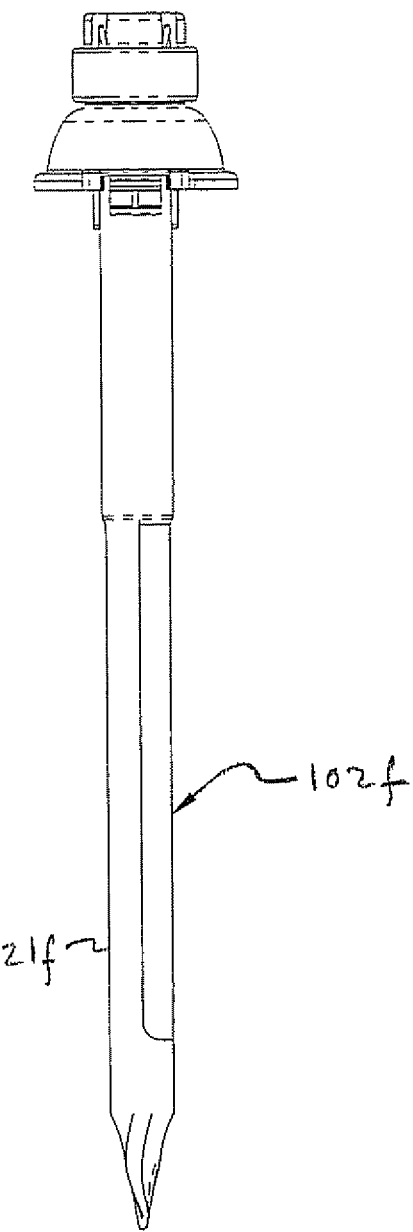
FIG. 19 illustrates a side view of a bladeless obturator of the invention and a cover for the cutout section of the shaft of FIG. 18.

Referring to FIG. 19, there is shown a cover 102f that can be attached over the cutout portion 100f of the ½-circle shaft 21f as shown in FIG. 18. In particular, a polycarbonate cover also with a ½-circle shaped cross-section can be attached to the shaft to form a tubular cross-section. An advantage of molding the tubular shaft 21f in two pieces is increased manufacturability of the shaft 21f. The cover 102f can be attached to the shaft 21f with an adhesive bond, an ultrasonic weld, a snap-fit, or with a shrink tube.

In another aspect, the obturator can be formed from two clam-shell components each including one-half of the shaft and tip configuration along the axial axis of the obturator. The two components can then be affixed together using an adhesive bond, an ultrasonic weld, an outer shrink tube, or a snap fit.

Referring to FIGS. 20 and 21, another feature of the bladeless obturator 18 of the invention is it is designed to frictionally lock the laparoscope 30 in place using a laparoscope lock 40, which can be formed within the handle 25. More specifically, the laparoscope lock 40 prevents the laparoscope 30 from moving axially relative to the shaft 21 of the obturator 18 during handling within the sterile field and during insertion through a body wall but enables the laparoscope 30 to rotate freely relative to the shaft 21. This rotation of the lock 40 enables the trocar system 10 to be twisted during insertion into and through the abdominal wall while maintaining the laparoscope 30 in a fixed rotational position that provides for a stable viewing image on the video monitor.

The conventional obturators with visualization properties include means for locking the laparoscope in place but these obturators lock the laparoscope both axially and rotationally. A drawback of the conventional devices is the viewing image on the video monitor is unstable if the trocar is twisted during insertion. More specifically, with prior art obturator laparoscope locks, if the trocar is twisted back and forth in a clockwise and counter-clockwise fashion, the laparoscope also moves clockwise and counter-clockwise with the trocar resulting in an oscillating and disorienting viewing image on the video monitor. The laparoscope lock 40 of the present invention improves visualization and enables a more precise placement of the trocar within the body tissue and across the body wall as compared to obturators of the prior art while preventing inadvertent axial movement of the laparoscope during handling and use.

Figures 22, 23:
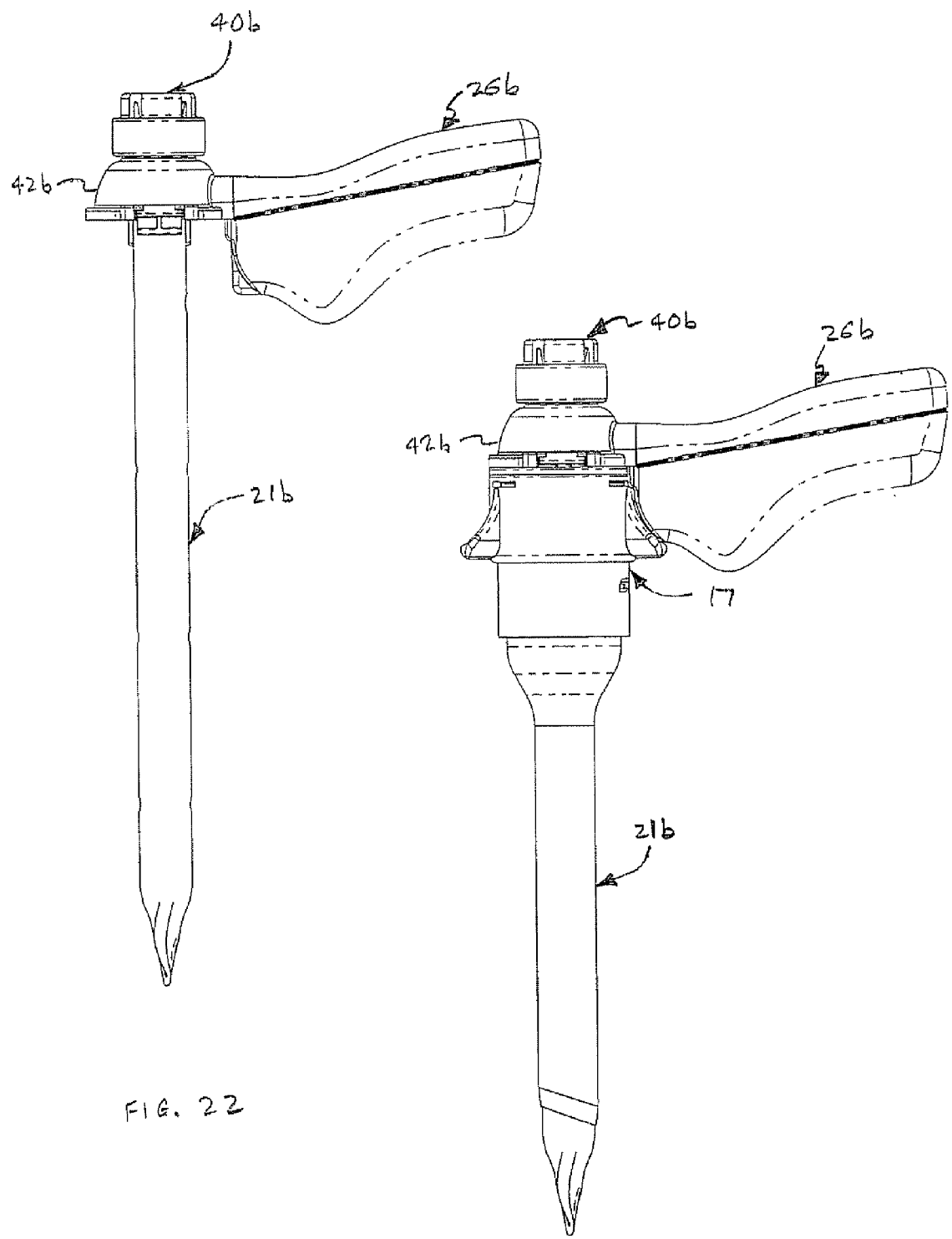
FIGS. 22 and 23 illustrate side views of a bladeless obturator of the invention including a cap with pistol-grip handle.

In another aspect of the invention as illustrated in FIGS. 20 and 21, the bladeless obturator 18 further comprises a cap 42 that can be snap-fitted onto the proximal end of the obturator shaft 21, after which the laparoscope lock 40 can be snap-fitted onto the end of the cap 42. Both the cap 42 and the lock 40 can be formed of a plastic material such as polycarbonate. The obturator cap 42 can be provided with and without a pistol-grip handle. The handled version of the bladeless obturator provides a pistol-grip to ease insertion of the trocar system as illustrated in FIGS. 22 and 23. The pistol-grip handle is designed to nest into the handle on the trocar seal to prevent excessive flexure of the handle during insertion of the trocar as illustrated in FIG. 23. More particularly, the handled bladeless obturator includes three components comprising of an obturator shaft 21b, an obturator cap 42b having a pistol-grip handle 26b, and a laparoscope lock 40b, all of which can be injection molded out of polycarbonate. The pistol-grip handle 26b can be formed with two components frictionally fitted together with, for example, interference pins. The interference pins can be fitted into holes in the handle 26b to affect a frictional lock between the two components.

Figure 24:
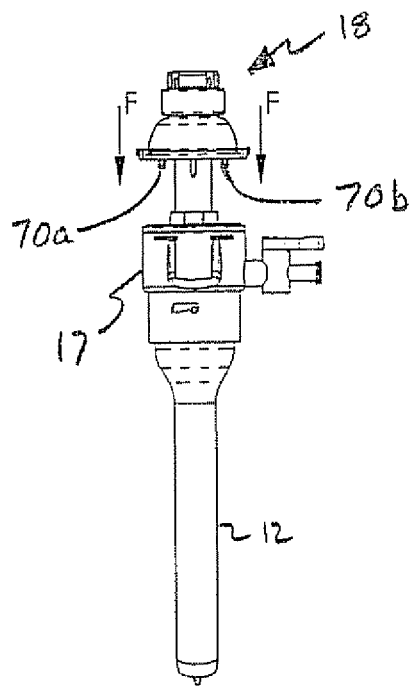
FIGS. 24 and 25 illustrate the locking mechanism between the bladeless obturator and the trocar seal of the invention.
Figure 25:
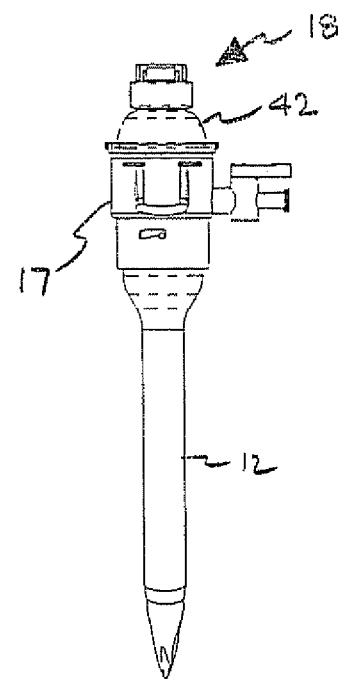
Figure 26:
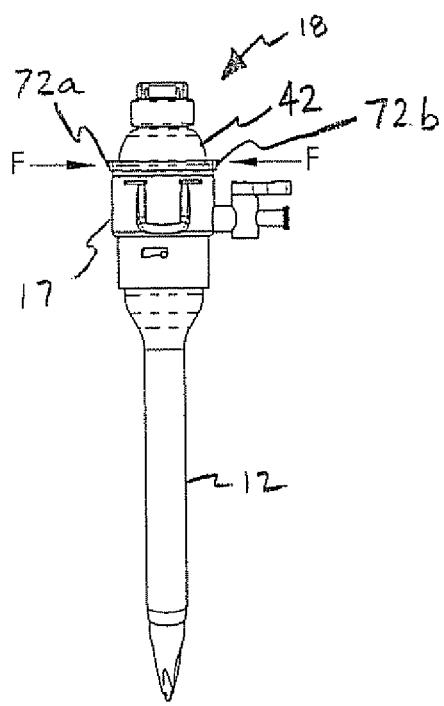
FIGS. 26 and 27 illustrate the release mechanism between the bladeless obturator and the trocar seal of the invention.
Figure 27:
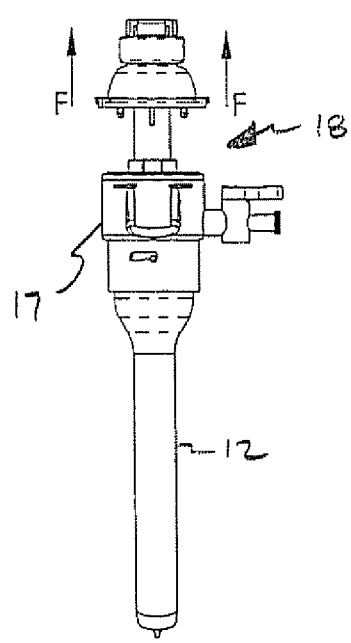

Referring to FIG. 24, the bladeless obturator 18 is designed to releasably attach to a trocar seal 17 via two cantilever snap-fits 70a, 70b. As the obturator 18 is inserted into the trocar seal 17 and cannula 12, the snap-fits 70a, 70b passively engage the trocar seal 17 and serve to axially lock the obturator 18 to the trocar seal 17 and cannula 12 (FIGS. 24 and 25). To release the obturator 18 from the trocar seal 17 and cannula 12, outboard tabs 72a, 72b on the obturator cap 42 are depressed inwardly and the obturator 18 is then free to be slidably removed as illustrated in FIGS. 26 and 27. Referring back to FIGS. 20 and 21, the bladeless obturator 18 includes axial key members 74 at its proximal end which are designed to mate with axial keyways on the trocar seal 17. As the bladeless obturator 18 is inserted into the trocar seal 17 and cannula 12, the obturator 18 is rotated slightly to align the axial key members 74 with the axial keyways and then advanced until the snap-fits 70a, 70b engage the trocar seal 17. The axial key members 74 serve to rotationally lock the obturator 18 to the trocar seal 17.

Figure 28:
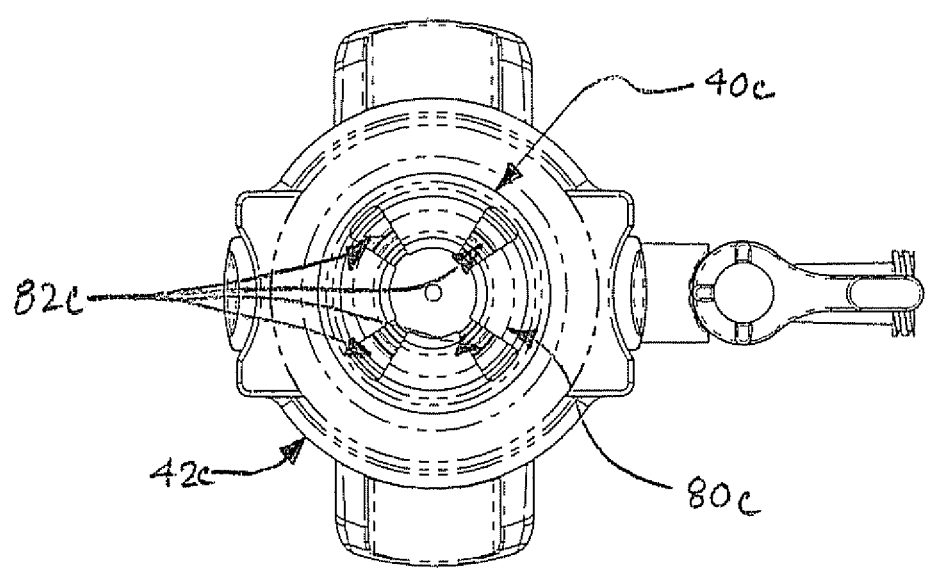
FIG. 28 illustrates a top view of a laparoscope lock of the invention comprising a multiple-finger collet.

Referring to FIG. 28, there is shown another embodiment of the laparoscope lock 40c comprising a multiple-finger collet 80c comprising a plurality of fingers 82c. The multiple-finger collet 80c has an inner diameter that is smaller than the outer diameter of the laparoscope. The fingers 82c of the collet 80c spread open during insertion of the laparoscope providing frictional engagement with the outer diameter of the laparoscope. The laparoscope lock 40c is free to rotate on an obturator cap 42c, and allows the laparoscope to freely rotate relative to the shaft of the bladeless obturator.

Referring back to FIGS. 20 and 21, the obturator shaft 21 of the bladeless obturator 18 can be configured with a barb 76 at its proximal end. The barb 76 is vertically slotted to enable the shaft 21 to flex during assembly. The obturator shaft 21 may also include a plurality of keys (not shown) near its proximal end. The obturator cap 42 is configured to axially slide over the barb 76 on the obturator shaft 21 to affect a one-way snap-fit lock between the two components. This snap-fit prevents the removal of the obturator cap 42 from the obturator shaft 21. The obturator cap 42 may further include keyways (not shown) that engage the keys on the obturator shaft 21 to rotationally index the components together. The obturator cap 42 may further include a second barb (not shown) at its proximal end. The laparoscope lock 40 may include a plurality of tabs (not shown) that are designed to spread and axially slide over the second barb on the obturator cap 42 to affect a one-way snap-fit lock between the obturator cap 42 and the laparoscope lock 40. This snap-fit prevents the axial removal of the laparoscope lock 40 from the obturator cap 42. The laparoscope lock 40 is free to rotate relative to the obturator cap 42.

Figure 29:
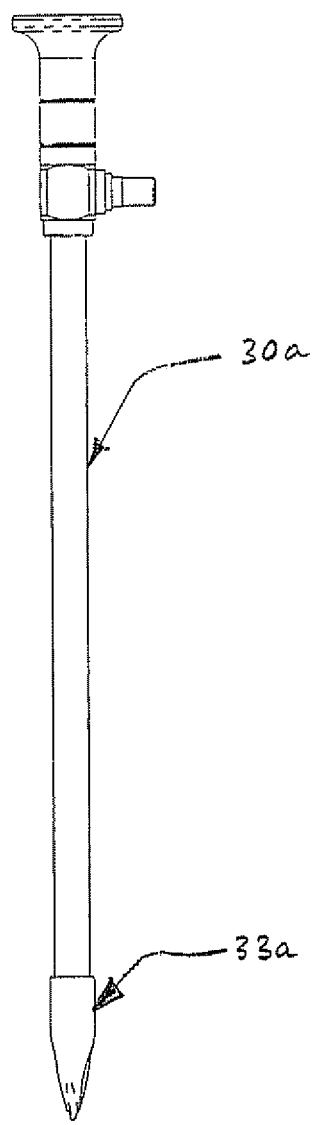
FIG. 29 illustrates an optical instrument having a transparent bladeless tip of the invention.

Referring to FIG. 29, there is shown another aspect of the invention of a laparoscope 30a having a tip 33a configured similar to that of the tip 27 of the bladeless obturator 18 described above, the tip 33a being adapted to snap-fit or frictionally engage the end of the laparoscope 30a. With this configuration, the combination of the tip 33a and the laparoscope 30a serve to form an optical obturator having a blunt tip. Once the trocar is inserted and the laparoscope removed from the trocar seal and cannula, the bladeless tip 33a can then be removed from the laparoscope 30a. The bladeless tip 33a can be formed from either a disposable or reusable transparent material. The bladeless tip 33a can be temporarily or permanently affixed to the scope 30a by any of the known methods of attaching the two components together as explained above.

Figure 30:
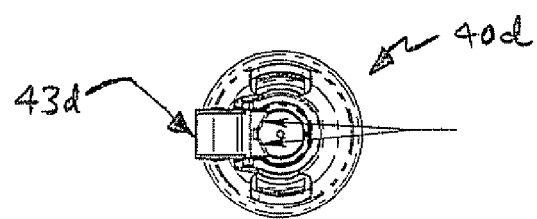
FIGS. 30 and 31 illustrate a top view and a side view, respectively, of a laparoscope lock of the invention comprising a camming member.
Figure 31:
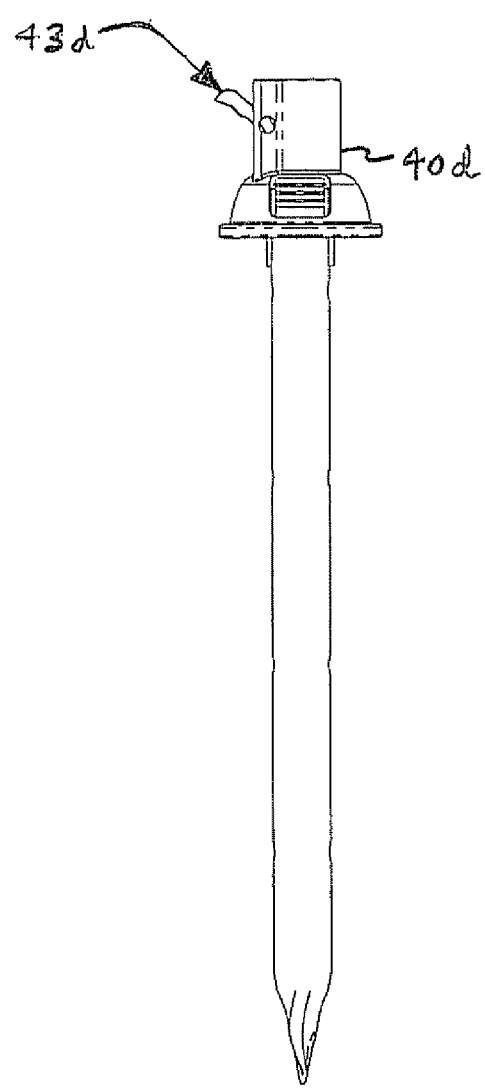
Figure 32:
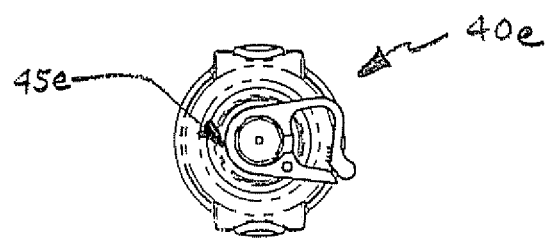
FIGS. 32 and 33 illustrate a top view and a side view, respectively, of a laparoscope lock of the invention comprising a clamping member.
Figure 33:
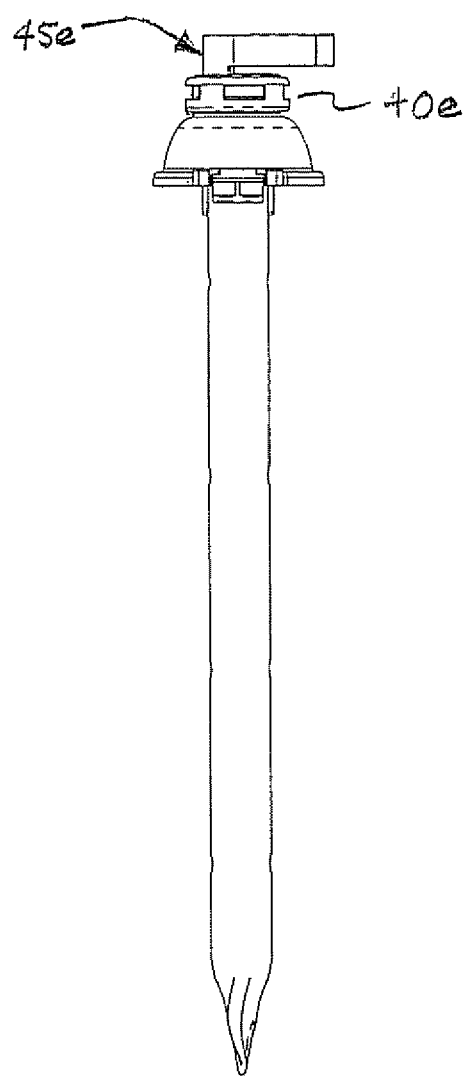

Referring to FIGS. 30 and 31, there is shown a laparoscope lock 40d in accordance with another embodiment of the invention including an active lock comprising a camming member 43d. With this type of lock, the laparascope would first be inserted into the shaft of the obturator and then the lock 40d would be activated to lock the laparoscope in an axial position relative to the shaft. The lock 40d can either rotate freely to enable the laparoscope to rotate freely relative to the shaft or the lock 40d can be rotationally fixed to prevent the laparoscope from rotating relative to the shaft. In another aspect as illustrated in FIGS. 32 and 33, a lock 40e can include an active lock comprising a clamping member 45e. With this type of lock, the laparascope would first be inserted into the shaft of the obturator and then the lock would be activated to lock the laparoscope in an axial position relative to the shaft. The lock 40e can either rotate freely to enable the laparoscope to rotate freely relative to the shaft or the lock 40e can be rotationally fixed to prevent the laparoscope from rotating relative to the shaft.

Figure 34:
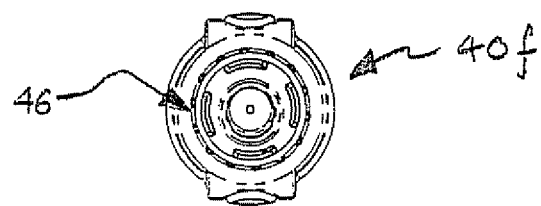
FIGS. 34 and 35 illustrate a top view and a side view, respectively, of a laparoscope lock of the invention comprising a locking collar.
Figure 35:
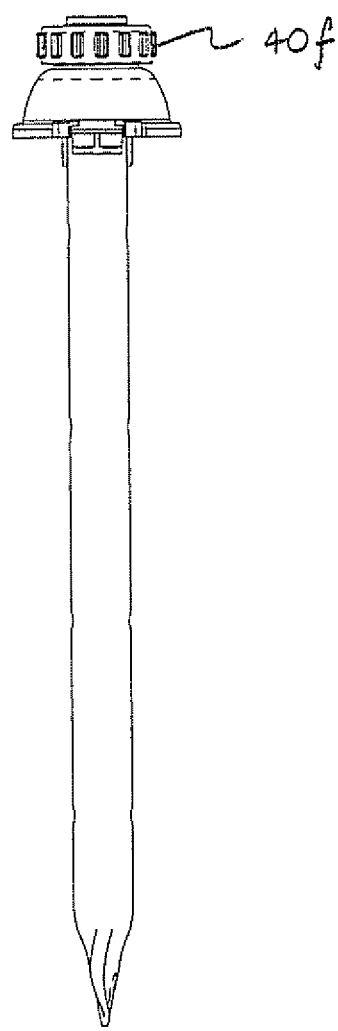

Referring to FIGS. 34 and 35, there is shown a lock 40f in accordance with another embodiment of the invention including an active lock comprising a locking collar 46 positioned eccentrically with respect to the axis of the obturator so that as the locking collar 46 is turned, a frictional engagement with the laparoscope is affected. The laparoscope would first be inserted into the locking collar 46 and the shaft of the obturator, the locking collar 46 can then be turned to frictionally engage the laparoscope. The laparoscope lock 40f can either rotate freely to enable the laparoscope to rotate freely relative to the shaft or the laparoscope lock 40f can be rotationally fixed to prevent the laparoscope from rotating relative to the shaft.

Figure 36:
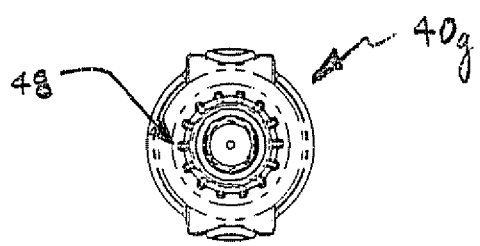
FIGS. 36 and 37 illustrate a top view and a side view, respectively, of a laparoscope lock of the invention comprising a locking nut and thread.
Figure 37:
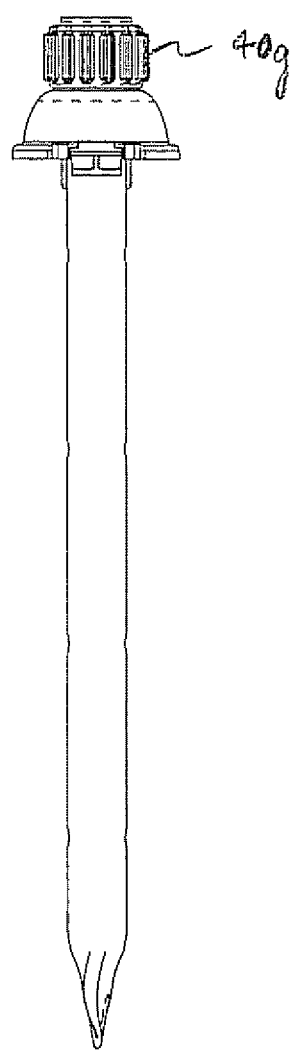

In another aspect of the invention as illustrated in FIGS. 36 and 37, there is shown a laparoscope lock 40g including an active lock comprising of a locking nut 48 and a thread. The threaded portion of the lock 40g has flexible elements similar to those on a collet. The laparoscope would first be inserted into the threaded portion of the lock 40g and the nut then rotated clockwise to collapse the flexible elements to frictionally engage the laparoscope. To release the laparoscope, the nut is rotated counter-clockwise.

In another aspect, the laparoscope lock can include a lock that includes an elastomeric element. The addition of the elastomeric element can enhance the frictional engagement with the laparoscope. An example of such an elastomeric element is a silicone O-ring sized with an inside diameter smaller than the outside diameter of the laparoscope. The laparoscope lock can either rotate freely to enable the laparoscope to rotate freely relative to the shaft or the laparoscope lock can be rotationally fixed to prevent the laparoscope from rotating relative to the shaft.

In yet another aspect, the obturator 18 can also be used as an insufflation needle having a passageway and valve to administer carbon dioxide or other insufflation gas to the peritoneal cavity. The obturator 18 can also be used with an insufflation needle cannula in which case removal of the obturator 18 upon entry would allow for rapid insufflation of the peritoneal cavity.

In another aspect of the invention, the bladeless obturator can be formed with a 2-3 mm outer diameter and with a small thru-hole at its distal end. The bladeless obturator can be used in conjunction with a miniaturized laparoscope to provide initial access into a hollow body cavity. Once access is obtained, the laparoscope can be removed from the bladeless obturator and an insufflation gas such as carbon dioxide can be dispensed through the obturator into the hollow body cavity. The bladeless obturator can also include holes in the tip portion to enhance the flow of insufflation gases though the obturator. More particularly, the bladeless obturator can be formed with a 2-3 mm outer diameter and used in conjunction with a miniaturized laparoscope to provide initial access into a hollow body cavity. After access is obtained, the bladeless obturator can be removed from the trocar cannula and an insufflation gas such as carbon dioxide can be dispensed though the cannula and into the hollow body cavity.

It will be understood that many modifications can be made to the disclosed embodiments without departing from the spirit and scope of the invention. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments.

We claim:

1. A surgical access device comprising:
an obturator comprising:
an elongate shaft extending along a longitudinal axis between a proximal end and a distal end; the elongate shaft defining a first lumen and having an opening at the proximal end; the first lumen having a first lumen diameter that is sized and configured to receive an optical instrument having a distal end adapted to receive an image; and
a transparent distal tip disposed at the distal end of the elongate shaft and adapted to permit passage of an image; at least part of the distal tip having a generally tapered configuration and an outer surface adapted for penetrating tissue;
an elastomeric element disposed at the proximal end of the elongate shaft; the elastomeric element having an inner diameter that is smaller than the first lumen diameter of the elongate shaft; the elastomeric element being configured to frictionally engage an optical instrument inserted into the first lumen and restrain the optical instrument inserted into the first lumen from moving axially relative to the obturator.

2. The surgical access device of claim 1 wherein the elastomeric element is an O-ring.

3. The surgical access device of claim 1 wherein the elastomeric element comprises a lock that rotates freely to enable the optical instrument to rotate freely relative to the shaft portion.

4. The surgical access device of claim 1 wherein the elastomeric element comprises a lock that is rotationally fixed to prevent the optical instrument from rotating relative to the shaft portion.

5. The surgical access device of claim 1 wherein the distal tip is hollow to receive the distal end of the optical instrument.

6. The surgical access device of claim 1 further including a cannula comprising an elongate shaft extending along a longitudinal axis and defining a second lumen between an open proximal end and an open distal end; the cannula configured to receive the obturator inside the second lumen.

7. The surgical access device of claim 6 further including a trocar seal located at the proximal end of the cannula; the trocar seal being configured for the insertion of the obturator.

8. The surgical access device of claim 1 further including at least one hole in the distal tip wherein the at least one hole in the distal tip is configured for delivering insufflation gases through the obturator and out the at least one hole.

9. A surgical access device comprising:
an obturator comprising:
an elongate shaft extending along a longitudinal axis between a proximal end and a distal end; the elongate shaft defining a first lumen and having an opening at the proximal end; the first lumen having a first lumen diameter that is sized and configured to receive an optical instrument having an outside diameter and a distal end adapted to receive an image; and
a transparent distal tip disposed at the distal end of the elongate shaft and adapted to permit passage of an image; at least part of the distal tip having a generally tapered configuration and an outer surface adapted for penetrating tissue; and
an elastomeric element disposed at the proximal end of the elongate shaft; the elastomeric element having an inner diameter that is smaller than the outside diameter of the optical instrument; the elastomeric element being in direct contact with the optical instrument when inserted in the first lumen and frictionally engaging the optical instrument to restrain movement of the optical instrument in the axial direction relative to the elongate shaft.

10. The surgical access device of claim 9 wherein the elastomeric element is an O-ring.

11. The surgical access device of claim 9 wherein the elastomeric element comprises a lock that rotates freely to enable the optical instrument to rotate freely relative to the shaft portion.

12. The surgical access device of claim 9 further including a cannula comprising an elongate shaft extending along a longitudinal axis and defining a second lumen between an open proximal end and an open distal end; the cannula configured to receive the obturator inside the second lumen.

13. The surgical access device of claim 9 further including at least one hole in the distal tip wherein the at least one hole in the distal tip is configured for delivering insufflation gases through the obturator and out the at least one hole.

14. The surgical access device of claim 9 wherein the optical instrument is a laparoscope and the distal end of the laparoscope when inserted extends into the hollow chamber of the distal tip.

* * * * *